(12) United States Patent
Lasmezas et al.

(10) Patent No.: US 9,612,238 B2
(45) Date of Patent: Apr. 4, 2017

(54) HIGH-THROUGHPUT SCREENING FOR COMPOUNDS MODULATING EXPRESSION OF CELLULAR MACRO-MOLECULES

(71) Applicant: THE SCRIPPS RESEARCH INSTITUTE, La Jolla, CA (US)

(72) Inventors: Corinne Lasmezas, Palm Beach Gardens, FL (US); Charles Weissmann, Palm Beach, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/046,483

(22) Filed: Oct. 4, 2013

(65) Prior Publication Data

US 2014/0039156 A1 Feb. 6, 2014

Related U.S. Application Data

(63) Continuation-in-part of application No. PCT/US2012/032587, filed on Apr. 6, 2012.

(60) Provisional application No. 61/472,962, filed on Apr. 7, 2011.

(51) Int. Cl.
*G01N 33/543* (2006.01)
*G01N 33/542* (2006.01)

(52) U.S. Cl.
CPC ......... *G01N 33/543* (2013.01); *G01N 33/542* (2013.01)

(58) Field of Classification Search
None
See application file for complete search history.

(56) References Cited

U.S. PATENT DOCUMENTS

| 6,040,194 A * | 3/2000 | Chick ................ A61K 49/0004 |
| | | 422/82.07 |
| 6,410,340 B1 * | 6/2002 | Soldin ........................... 436/503 |
| 2005/0042208 A1 * | 2/2005 | Sagawa ................ C12N 5/0636 |
| | | 424/93.7 |
| 2008/0108096 A1 | 5/2008 | Ralph |
| 2010/0070191 A1 | 3/2010 | Gold et al. |
| 2012/0040337 A1 * | 2/2012 | Unger et al. ...................... 435/5 |

OTHER PUBLICATIONS

Goedken et al. J. Biomolecular Screening 2008 vol. 13, p. 619-625.*
Kong et al. 2006 Cancer Res. vol. 66, p. 2834-2843.*
Degorce, Francois, et al., "HTRF: A Technology Tailored for Drug Discovery—A Review of Theoretical Aspects and Recent Applications," Current Chemical Genomics, 2009, 3, pp. 22-32.

* cited by examiner

*Primary Examiner* — Jacob Cheu
(74) *Attorney, Agent, or Firm* — McHale & Slavin, P.A.

(57) ABSTRACT

A method of screening for compounds that module expression of specific macromolecules, the "target". The method is particularly useful in that it does not require separation of target-bound and excess ligand and therefore enables, but is not limited to, High Throughput Screening for compounds that increase or decrease the levels or amounts of a target present in a biological sample. The method can also be used for high-throughput diagnosis of a condition leading to an increase or decrease of a cellular macromolecule.

32 Claims, 6 Drawing Sheets

A.
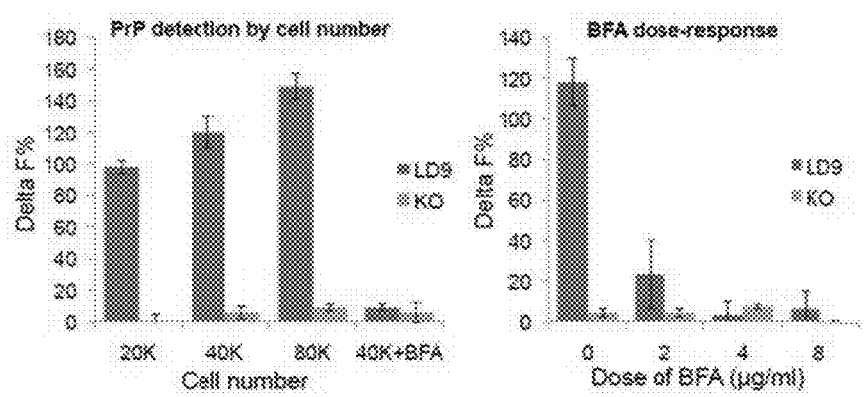
C.
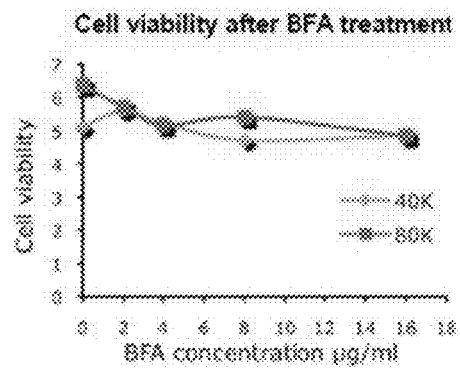
FIGURES 1A-1C

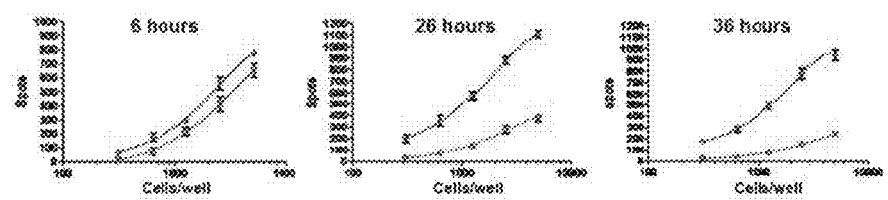
FIGURE 6
A  RML infection of PK1 cells
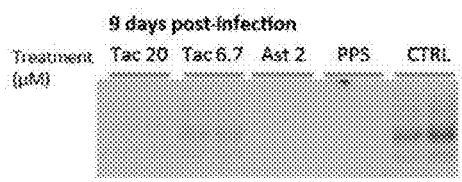
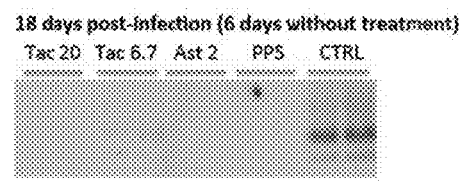
B  22L infection of PK1 cells
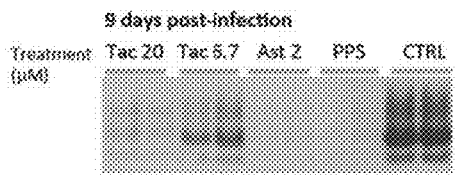
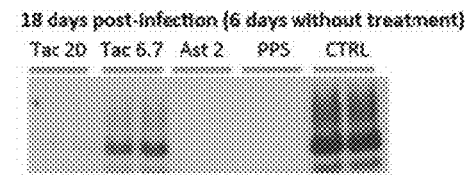
FIGURES 7A, 7B

HIGH-THROUGHPUT SCREENING FOR COMPOUNDS MODULATING EXPRESSION OF CELLULAR MACRO-MOLECULES

CROSS-REFERENCE TO RELATED APPLICATIONS

The present application is a Continuation-In-Part of International Application No. PCT/US2012/032587, filed Apr. 6, 2012, which claims priority to U.S. Provisional Patent Application No. 61/472,962, entitled "HIGH-THROUGH-PUT SCREENING FOR COMPOUNDS MODULATING LEVELS OF CELLULAR MACROMOLECULES" filed Apr. 7, 2011, which is incorporated herein by reference in its entirety.

FIELD OF THE INVENTION

Embodiments are directed to methods for the quantification of specific cellular components ("targets") by a FRET-based assay which does not require attachment of the targets to a solid phase nor the separation of the target from excess reagents, making it suitable for high-throughput screening.

BACKGROUND

Quantification of a specific macromolecule (the "target"), particularly in the presence of other components, such as, a specific protein on the cell surface, in a protein mixture, in a cell homogenate, is commonly performed with use of an antibody that specifically recognizes the target. In general, the protein mixture is first immobilized on a support, for example, by adsorption or covalent linkage to a membrane or a plastic surface, or to a support surface to which an antibody specific for the target ("immobilizing antibody") has been attached, and exposed to a target-specific antibody ("primary antibody", different from the immobilizing antibody, if one was used). After an appropriate reaction time, excess primary antibody is removed by repeated washes, and the amount of bound antibody is determined by one of several methods. For example, the primary antibody may have been covalently linked to a fluorescent tag, and may be detected by measuring the intensity of fluorescence; alternatively, a "secondary" antibody (tagged with a marker, such as a fluorescent dye or an enzyme) directed against the primary antibody, may be used for quantification. Many different approaches for the quantification of the primary antibody are available, but common to all is the requirement that any primary or secondary antibody that is not bound to the target be completely removed, because it would give rise to a signal indistinguishable from that of specifically bound antibody. Because high-throughput screening does not allow for washing steps, the above-mentioned approaches are not applicable.

SUMMARY

This Summary is provided to present a summary of the invention to briefly indicate the nature and substance of the invention. It is submitted with the understanding that it will not be used to interpret or limit the scope or meaning of the claims.

Embodiments are directed to a method of screening, in particular in a high throughput mode, in a homogeneous or heterogeneous solution for compounds modulating expression of a specific macromolecule, the "target", including but not restricted to a specific protein or nucleic acid. In a preferred embodiment, at least two target-specific, FRET-enabling ligands, are directed against at least two specific, distinct sites on the macromolecule, one ligand being linked to at least one donor fluorophore and the other to at least one acceptor fluorophore. Examples of FRET-enabling ligands, include but are not restricted to: antibodies, antibody mimetics, peptoids, peptide or nucleic acid aptamers. The embodiments enable high throughput screening of compounds able to modify the amounts of a specific macromolecule in a biological sample. Further, the embodiments enable high throughput identification and quantification of a specific macromolecule in a biological sample.

Other aspects are described infra.

BRIEF DESCRIPTION OF THE DRAWINGS

FIGS. 1A-1B are graphs showing PrP detection at the surface of living LD9 cells using the PrP detection assay in the 96-well format. PrP knock-out cells (KO) lacking expression of PrP are used as a negative control. PrP levels are expressed as [Delta F %] which is a value resulting from the ratiometric measurement of the HTRF signal corresponding to the detection of PrP. FIG. 1A: PrP detection as a function of cell number and effect of the treatment with brefeldine A (BFA). Z' is a statistical parameter measuring the quality of an assay (Z'>0.5 is considered an excellent assay). Z' of the assay was 0.7 when 20K or 40K LD9 cells were used, and 0.8 for 80K LD9 cells. FIG. 1B: PrP detection after treatment of LD9 cells with increasing doses of BFA during 24 hours; 4 and 8 µg/ml reduce the PrP signal to background. Triplicates are shown. FIG. 1C shows that none of the tested doses of BFA were toxic to LD9 cells. Cell viability was measured using the CELLTITER-GLO® luminescent assay (Promega) in singlicate.

FIGS. 4A, 4B: microscopic analysis of N2a cells treated with DMSO (left picture) and Tacrolimus (right picture). Quantification was performed by flow cytometry (FIG. 4C) and IN Cell analyzer 1000 with Developer software (FIG. 4D). Key for FIG. 4C: red: PrP signal of the negative control (secondary antibody alone); blue: PrP signal for the positive control (DMSO treated cells); green and orange: duplicate analysis of PrP signal for the cells treated with Tacrolimus at three different doses indicated in the panels.

FIG. 6 shows a secondary assay used to prioritize hits reducing cell surface PrP expression. The graphs represent the number of infected cells (detected as spots by the scrapie cell assay—SCA) as a function of cell number. Blue lines: untreated cells; Red lines: cells treated with 1 µg/ml PIPLC (for the time indicated on each panel). The "$RI_{200}$" value is defined as the reciprocal of the cell number required to give 200 spots. The $RI_{200}$ for control PK1 [RML] at 26 hours is $3.3 \times 10^{-3}$ and for PIPLC-treated PK1 [RML] it is $5 \times 10^{-4}$. Therefore PIPLC caused a 85% inhibition of infection $(1-[5 \times 10^{-4}/3.3 \times 10^{-3}] \times 100)$.

FIGS. 7A and 7B illustrate that tacrolimus (Tac) and astemizole (Ast), two compounds screened using the method described herein that reduce cell surface PrP amounts as shown in FIGS. 4A-4D and 5A-5B, block infection of PK1 neuroblastoma cells by RML and 22L prions. PK1 cells were pretreated for 3 days with the indicated doses of drugs and infected with RML (FIG. 7A) or 22L (FIG. 7B) prions using a $10^{-4}$ dilution of brain homogenate from an RML- or 22L-infected mouse. Treatment was continued for 12 days after infection. Cells were analyzed by western blot for proteinase K-resistant $PrP^{Sc}$ (a hallmark of prion infection) 9 and 18 days post-infection (i.e. 3 days before and 6 days after treatment cessation). PPS (pentosan polysulfate), a drug that prevents prion infection, was used at the dose of 10 µg/ml as positive control for treatment efficacy. CTRL: untreated cells. Both astemizole and tracrolimus blocked prion infection, and there was no rebound of infectivity after treatment cessation.

FIGS. 8A, 8C: non-treated cells. FIGS. 8B, 8D: cells exposed to Aβ42 oligomers for 4 days (100 µg/ml). In FIG. 8B, cell vacuolation and loss was observed. FIG. 8E is a Western-blot analysis in triplicate showing PrP expression only in SK-NSH cells.

FIG. 9A: Tau detection in SH-SY5Y cells as a function of cell number. Z' is a statistical parameter measuring the quality of an assay (Z'>0.5 is considered an excellent assay). Z' of the assay was 0.7 when 18K or 24K SH-SY5Y cells were used. Triplicates are shown. Error bars correspond to standard deviations. FIG. 9B: Tau knockdown in SH-SY5Y cells using RNA interference leads to a specific decrease in tau detection. Triplicates are shown. Error bars correspond to standard deviations. FIG. 9C: Tau detection in SK-NSH cells after treatment with increasing doses of staurosporine (in 0.75% DMSO final) or 0.75% DMSO alone (CTRL) during 24 hours using the tau detection assay in the 384-well format. [Delta F %] was calculated using medium containing 0.75% DMSO as blank (average signal from 16 wells). Z' of the assay was 0.5. Bars correspond to the average signal from 8 wells (each dose of staurosporine) or 96 wells (CTRL). Error bars correspond to standard deviations.

DETAILED DESCRIPTION

Figure 2:
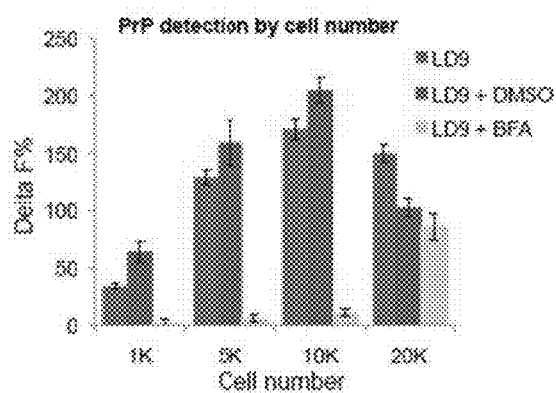
FIG. 2 is a graph showing PrP detection at the surface of living LD9 cells using the PrP detection assay described in the 384-well format. DMSO is the solvent used in most small molecules screening libraries and will be used as a control in the screening plates. Therefore the Z' is calculated using LD9+DMSO as control for the highest PrP signal, LD9+ BFA as control for the lowest PrP signal. Z' of the assay was 0.4, 0.6, 0.8 and −2.7 for $10^3$, $5\times10^3$, $10^4$ and $2\times10^4$ of LD9 cells, respectively. Each point was done in triplicate.

Embodiments are directed to methods for the efficient screening, identification and quantification of samples containing target molecules for use in High-Throughput Screening (HTS) assays. In particular, the assays described herein do not require washing steps nor the attachment of the target molecules to solid supports. Thus, the targets can be assayed under conditions where they retain their natural, in vivo, conformation. Novel compounds or new uses of known compounds that affect the level of a cellular macromolecule can be identified.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "specific binding" or "specifically binding" when used in reference to the interaction of a protein and an antibody or alternative protein scaffold or peptoid or aptamers, means that the interaction is dependent upon the presence of a particular structure (i.e., the antigenic determinant or epitope) on the protein; in other words the antibody is recognizing and binding to a specific protein structure rather than to proteins in general. Thus, an antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The term "ligand," includes any compound, composition or molecule capable of specifically or substantially specifically (that is with limited cross-reactivity) binding another compound or molecule, which, in the case of immune-recognition contains an epitope. In many instances, the ligands are antibodies, such as polyclonal or monoclonal antibodies. "Ligands" also include derivatives or analogs of antibodies, including without limitation: Fv fragments; single chain Fv (scFv) fragments; Fab' fragments; F(ab')$_2$ fragments; humanized antibodies and antibody fragments; camelized antibodies and antibody fragments; and multivalent versions of the foregoing. Multivalent binding reagents also may be used, as appropriate, including without limitation: monospecific or bispecific antibodies, such as disulfide stabilized Fv fragments, scFv tandems ((scFv)fragments), diabodies, tribodies or tetrabodies, which typically are covalently linked or otherwise stabilized (i.e., leucine zipper or helix stabilized) scFv fragments. "Ligands" also include peptoids, peptide or nucleic acid aptamers, or antibody mimetics such as DARPins, affibody molecules, affilins, affitins, anticalins, avimers, fynomers, recombinant probes, Kunitz domain peptides and monobodies.

A "label" or a "detectable label" is a composition detectable by spectroscopic, photochemical, biochemical, immunochemical, chemical or any other means. For example, useful labels include radio labeled molecules, fluorophores, luminescent compounds, electron-dense reagents, enzymes (e.g., as commonly used in an ELISA), biotin, digoxigenin, or haptens and proteins which can be made detectable, e.g., by incorporating a label into the peptide or used to detect antibodies specifically reactive with the peptide.

The term "fluorophore" includes any compound, composition or molecule capable of emitting light in response to irradiation. In many instances, fluorophores emit light in the visible region of light. In other instances, the fluorophores can emit light in the non-visible regions of light, such as ultraviolet, near-ultraviolet, near-infrared, and infrared. For example and without limitation, examples of fluorophores include: quantum dots; nanoparticles; fluorescent proteins, such as green fluorescent protein and yellow fluorescent protein; heme-based proteins or derivatives thereof; carbocyanine-based chromophores, such as IRDye 800CW, Cy 3, and Cy 5; coumarin-based chromophores, such as (7-diethylamino-3-(4'-maleimidylphenyl)-4-methylcoumarin) (CPM); fluorine-based chromophores, such as fluorescein, fluorescein isothiocyanate (FITC); and numerous ALEXA FLUOR™ chromophores and ALEXA FLUOR™ bioconjugates, which absorb in the visible and near-infrared spectra. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners).

As used herein, the term "chromophore" refers to a substituent which, with another chromophore, can be used for energy transfer (e.g., FRET assay).

The term "chemiluminescent compound" includes any compound, composition or molecule capable of emitting light in response to a chemical reaction. A "bioluminescent compound" refers to a naturally occurring form of a chemiluminescent compound. Examples of chemiluminescent compounds include: lucigenin, luminol. Examples of bioluminescent compounds include: luciferins, coelenterazines. The emission from chemiluminescent compounds can be detected by luminometers or scanning spectrometers.

The term "luminescent component" or "luminescent compound" as used herein refers to a component capable of absorbing energy, such as electrical (e.g., electro-luminescence), chemical (e.g., chemi-luminescence) or acoustic energy and then emitting at least some fraction of that energy as light over time. The term "component" as used herein includes discrete compounds, molecules, bioluminescent proteins and macro-molecular complexes or mixtures of luminescent and non-luminescent compounds or molecules that act to cause the emission of light.

"Sample" is used herein in its broadest sense. A sample comprising polynucleotides, polypeptides, peptides, antibodies and the like may comprise a bodily fluid; a soluble fraction of a cell preparation, or media in which cells were grown, a cell culture; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

As used herein, "biological samples" include solid and body fluid samples. The biological samples used in the present invention can include cells, cell cultures, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils, thymus and skin, or samples taken from tumors. Examples of "body fluid samples" include, but are not limited to blood, serum, semen, prostate fluid, seminal fluid, urine, feces, saliva, sputum, mucus, bone marrow, lymph, and tears.

The term "high-throughput screening" or "HTS" refers to a method drawing on different technologies and disciplines, for example, optics, chemistry, biology or image analysis to permit rapid, highly parallel biological research and drug discovery. HTS methods are known in the art and they are generally performed in multiwell plates with automated liquid handling and detection equipment; however it is envisioned that the methods of the invention may be practiced on a microarray or in a microfluidic system.

The term "library" or "drug library" as used herein refers to a plurality of chemical molecules (test compound), a plurality of nucleic acids, a plurality of peptides, or a plurality of proteins, organic or inorganic compounds, synthetic molecules, natural molecules, or combinations thereof.

As used herein, the term "target" or "target molecule" refers to any type of molecule, or structure to be detected or characterized. The molecule can be an intracellular molecule, such as for example, nucleic acid sequences, peptides, structures (e.g. intracellular membranes, ribosomes, etc.), surface molecules (e.g. receptors), extracellular molecules (e.g. cytokines, enzymes, viral particles, organisms, biological samples and the like.

A "polynucleotide" means a single strand or parallel and anti-parallel strands of a nucleic acid. Thus, a polynucleotide may be either a single-stranded or a double-stranded nucleic acid.

Unless otherwise indicated, the terms "peptide", "polypeptide" or "protein" are used interchangeably herein, although typically they refer to peptide sequences of varying sizes.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as "encoding" the protein or other product of that gene or cDNA.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

An "amount" or "quantity" of a molecule refers to the concentration, volume, mass, weight, percentage or any other factor that one of skill in the art would recognize as a means to measure how much of the molecule is present as compared to a baseline control. The amount can decrease or increase or remain the same as compared to the control. An example of measuring the amount of a molecule is shown in the examples section which follows.

By the term "modulate," it is meant that the amounts, activity, function, expression, of a molecule, e.g. PrP, tau etc., are, e.g., increased, enhanced, agonized, promoted, decreased, reduced, suppressed blocked, or antagonized. Modulation can increase amounts, activity, function, expression of a molecule more than 1-fold, 2-fold, 3-fold, 5-fold, 10-fold, 100-fold, etc., over baseline values. Modulation can also decrease its amounts, activity, function, expression below baseline values. Modulation can also normalize amounts, activity, function, expression to a baseline value.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

"Optional" or "optionally" means that the subsequently described circumstance may or may not occur, such that the description includes instances where the circumstance occurs and instances where it does not.

The terms "patient", "subject" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Assay Description.

In a preferred embodiment, the sample containing the protein or the desired molecule to be screened for (the "target") is placed into a receptacle. In one embodiment, the target is a known molecule, for example when screening for a particular molecule diagnostic of a disease or disorder or identifies subjects that may be at risk of developing a disease or disorder, or when screening for a compound that will modify the amount of a disease-associated molecule. The assay is termed herein as FRET-enabled high throughput assay (FEHTA). The assay specifically identifies and/or quantifies specific proteins in a sample and includes intracellular, extra-cellular or cell surface molecules. The assays embodied herein do not require the step of washing. In some embodiments, one or more washing steps can be omitted.

An example of the assay, which is meant to be illustrative and should not be construed as limiting, is provided. For example, the first ligand, which is linked to the donor fluorophore, and the second ligand which is linked to the acceptor fluorophore are added to the receptacle. Each of the ligands bind to a specific and distinct site on the same target molecule. The sample containing the target linked to the ligands is irradiated at a wavelength optimal for exciting the donor fluorophore. The intensity of the light emitted by the acceptor fluorophore as a result of its excitation by the energy transferred from the donor fluorophore (Förster Resonance Energy Transfer (FRET)) is measured. The distance between the donor fluorophore and the acceptor fluorophore is defined as being equal to or less than the distance defined by the Förster radius.

The samples can be identified and/or quantified by any useful fluorescence detection method, such as by fluorimeters, time-resolved fluorimeters, fluorescent microscopy, fluorescent plate readers, infrared scanner analysis, spectrophotometers, fluorescent-activated cell sorters (FACS), and fluorescent scanners (e.g., gel/membrane scanners). Although samples can be analyzed with a laser scanning confocal microscope, an automated confocal nannoscanner or a microplate spectrofluorimeter, the method can be easily adapted to other devices (i.e. FACS cell sorter) for applications in other fields. FRET can be detected directly or indirectly. Direct detection of FRET is performed exciting the donor (CPM) and detecting the signal emitted by the acceptor (FITC or Alexa488). As used herein the term "signal" means any detectable event (whether direct or indirect) indicative of FRET, and includes without limitation, emission of a photon. FRET is detected indirectly using the method described by Karpova and co-workers (T. S. Karpova et al., *J Microsc* 209, 56-70, 2003).

The term "assay" used herein, whether in the singular or plural shall not be misconstrued or limited as being directed to only one assay with specific steps but shall also include, without limitation any further steps, materials, various iterations, alternatives etc., that can also be used. Thus, if the term "assay" is used in the singular, it is merely for illustrative purposes.

In a preferred embodiment, the assay optionally omits or does not require washing between steps. In one aspect the washing steps are omitted before and/or after adding the ligands to the receptacles. The drawback with currently available assays is that the requirement that the target be firmly bound to a support raises two major problems: (a) binding may be incomplete, the efficiency of binding may be different for distinct conformations or forms of the target, or binding of the target to the support may mask to an unknown degree the accessibility of the site to be recognized by the primary antibody. (b) The requirement that excess antibody (both secondary and/or primary) be removed as completely as possible requires repeated washes, which is laborious and time-consuming, and in some cases not doable. In particular in High Throughput assays, where tens- or hundreds of thousands of samples are screened in 384 or 1536 well-plates, washing procedures cannot be implemented.

The assays (FEHTA) embodied herein, obviate the necessity of attaching the target to a support and of a washing step. In one embodiment, the assay employs Förster Resonance Energy Transfer or FRET, a process in which a fluorophore ("donor") that can be excited by light and can transfer the excitation to a second fluorophore ("acceptor") if and only if they are sufficiently close, that is, within a distance in the order of 100 Å or less, defined by the Förster radius. Further details regarding FRET assays are provided below. Although FRET is used as an illustrative example, the assays described herein are not limited to FRET based assays. For example, an assay which uses a bioluminescent protein, such as luciferase, to excite a proximal fluorophore (BRET), typically a fluorescent protein (Xu et al. (1999) *Proc. Natl. Acad. Sci.* USA 96(1), 151-6). Another assay alternative is a luminescent oxygen-channeling chemistry (Ullman et al. (1994) *Proc. Natl. Acad. Sci.* USA 91(12), 5426-30), wherein a light induced singlet oxygen generating system transfers the singlet oxygen to a chemiluminescent system in proximity.

In one embodiment, the donor and acceptor fluorophores (detectable label/detectable molecules) are attached to two distinct ligands, for example, antibodies that can bind specifically to distinct sites of one and the same target. When the ligands carrying the donor and the acceptor fluorophore, respectively, bind to the same target molecule and in doing so become sufficiently close to each other, inadiation of the sample at a wavelength that allows excitation of the donor results in emission of radiation by the acceptor. Ligands that are not bound to the same target do not give rise to FRET and therefore need not be removed prior to measurement of emitted radiation. Since the target is not adsorbed or bound to a support, it is fully available for interaction with the ligands.

In one embodiment, a method of identifying and quantifying a specific target molecule in a sample comprises screening a sample containing the specific target molecule in a high-throughput screening assay comprising the steps of: (i) adding a first and second ligand, each having a first and second detectable label, (ii) the first and second ligands each binding to separate and specific sites on a specific target molecule, wherein the screening assay optionally omits or does not require the step of (iii) washing, and detecting an emission of light when the first and second ligands specifically bind to the specific target molecule. Preferably, the detectable label comprises: fluorophores, luminescent molecules, enzymes or radionuclides. In some embodiments, the light comprises: fluorescence, chemiluminescence, or bioluminescence.

In some embodiments, the assay is a high-throughput screening assay wherein the high-throughput screening assay comprises a Förster Resonance Energy Transfer (FRET), Bioluminescence Resonance Energy Transfer (BRET), or fluorescence polarization assay.

In one embodiment, the ligands comprise: polypeptides such as antibodies or antibody fragments bearing epitope recognition sites, such as Fab, Fab', F(ab')$_2$ fragments, Fv fragments, single chain antibodies, antibody mimetics (such as DARPins, affibody molecules, affilins, affitins, anticalins, avimers, fynomers, Kunitz domain peptides and monobodies), recombinant probes, peptoids, aptamers and the like. In one embodiment the first and second ligands are the same type of molecule. In another embodiment, the first and second ligands are different types of molecules. In some embodiments, the first or second ligands comprise: antibodies, antibody fragments, Fv fragments; single chain Fv (scFv) fragments; Fab' fragments; F(ab')2 fragments, humanized antibodies and antibody fragments; camelized antibodies and antibody fragments, human antibodies and antibody fragments, monospecific or bispecific antibodies, disulfide stabilized Fv fragments, scFv tandems ((scFv)$_2$ fragments), diabodies, tribodies or tetrabodies, peptoids, peptide or nucleic acid aptamers, antibody mimetics or combinations thereof. In other embodiments, the first and second ligands comprise: a polypeptide, antibodies, antibody fragments, antibody mimetics, single chain antibodies, nucleic acids, an aptamer, a peptoid or a sugar moiety or combinations thereof. In certain embodiments, the first and second ligands are peptide or nucleic acid aptamers. In other embodiments, the first and second ligands are sugar moieties comprising glycosaminoglycans, heparan sulfates or chondroitin sulfates.

In some embodiments, the methods are used to identify and quantify a specific molecule in a sample. In such embodiments, a method of quantifying a specific molecule, e.g. a protein in a sample, the method comprises the steps of: placing the sample containing the specific target molecule into a receptacle permitting irradiation of the sample at a wavelength suitable for exciting the donor fluorophore and measurement of the fluorescence of the acceptor fluorophore via a high-throughput assay; adding a first ligand that binds to a specific site on the target molecule wherein the first ligand is linked to a first fluorophore (the "donor fluorophore"); adding a second ligand that binds to a specific site on the same target molecule distinct from that to which the first ligand binds wherein the second ligand is linked to a second fluorophore (the "acceptor fluorophore"); optionally, omitting washing steps between each step; irradiating the sample containing the target molecule linked to the ligands at a wavelength optimal for exciting the donor fluorophore and measuring the intensity of the light emitted by the acceptor fluorophore or both the donor and acceptor fluorophores. In embodiments, the assay is a high-throughput screening assay. In one embodiment the specific molecule is a prion protein (PrP). In another embodiment, the specific molecule is a Tau protein or peptides, or hyperphosphorylated tau molecules.

In one embodiment, the intensity of the light emitted is measured by time resolved fluorimetry. In embodiments, the excitation is transferred to the acceptor fluorophore when the acceptor fluorophore is at a distance from the donor fluorophore that is equal to or less than the distance defined by the Förster radius.

In embodiments, the target is present in a sample comprising: a liquid, a semi-liquid, a gel, a biological sample, an intact cell, a permeabilized cell, a disrupted cell, a cell homogenate, a membrane, or a cellular organelle.

In other embodiments, the ligands are linked to a detectable label (detectable molecule), either directly or linked via a suitable linker. The present invention is not limited to any particular linker group. Indeed, a variety of linker groups are contemplated, suitable linkers could comprise, but are not limited to, alkyl groups, ether, polyether, alkyl amide linker, a peptide linker, a polypeptide linker, a modified peptide or polypeptide linker, a peptide nucleic acid (PNA) a Poly (ethylene glycol) (PEG) linker, a streptavidin-biotin or avidin-biotin linker, polyaminoacids (e.g. polylysine), functionalized PEG, polysaccharides, glycosaminoglycans, dendritic polymers PEG-chelant polymers, oligonucleotide linker, phospholipid derivatives, alkenyl chains, alkynyl chains, disulfide, or a combination thereof.

In another preferred embodiment, the detectable label is linked to the ligand, through a chemical bond, or noncovalently, through ionic, van der Waals, electrostatic, or hydrogen bonds.

There are various methods that one of skill in the art can practice to identify various ligands or combinations of ligands. In one example, a best ligand pair analysis was carried out as described in the "Examples" section which follows. In addition, to select the best compounds from the hits generated during the primary screening, the following strategy can be used: (1). Selection of the compounds exerting the highest effect. (2). Selection of the compounds exerting the effect at the lowest concentration and harboring the least toxicity on cells. To this end, $EC_{50}$ and $TC_{50}$ can be determined by any of the assays routinely used by those of ordinary skill in the art. (3). Selection of the compounds exhibiting the highest specificity for a molecule. Although complete specificity is not required for a compound to achieve a good therapeutic index, this can be used as criteria for compound selection. (4). Selection of the compounds showing the highest of the desired property or therapeutic capacity can be determined. The "therapeutic capacity" (or "treatment") is dependent on the condition to be treated. For example, an anti-viral would inhibit a viral infection by either inhibiting replication, slowing growth of the virus, etc. Any desired output parameter can be used. An "effect" would be the type of parameter that one of skill in the art is screening the compounds for. This is inclusive of, for example, amount, activity, function, expression etc., of the target molecule. For example, the amounts of the target molecule can be due to upstream or downstream activities of other molecules which may modulate the amount of the target molecule. Thus, for example, if one of skill in the art is screening compounds for an inhibitory effect on a certain target molecule, then the parameters used, can be expression profiles if the target molecule is a nucleic acid peptide etc. In other cases it can be the activity, e.g. if it is an enzyme. In other cases it can be a receptor and the effect measured would be modulation of signaling, or surface expression, or conformation change. In other cases, the test compound or a candidate therapeutic agent, may have an effect on the formation or properties (e.g., conformation or binding affinity) between the target molecule and its binding partner. In other cases, the compound or test agent may have an effect on the secondary or tertiary structure of the target molecule. In other cases, the test agent may inhibit the function of the target molecule. Thus, the effects measured would be limited only by the imagination of the user.

In certain embodiments, provided herein are methods for identifying the effects of a compound that modulates amounts or quantities of a target molecule, comprising: (a) providing a target molecule labeled with a first chromophore at a first position; (b) exciting the chromophore; and (c) measuring the fluorescence lifetime of the first chromophore; wherein a difference between the fluorescence lifetime in the presence of the test compound and the fluorescence lifetime in the absence of the test compound indicates that the test compound modulates the target molecule, such that the fluorescence lifetime of the chromophore is altered. In one embodiment, the target molecule is further labeled with a second chromophore at a second position, wherein the second position is different from the first position, and wherein the chromophores can be used for energy transfer.

In certain embodiments, provided herein are methods for identifying the effects of a compound that modulates (e.g. amounts of) a target molecule, comprising: (a) providing a target molecule labeled with a first chromophore at a first position and a second chromophore at a second position, wherein the second position is different from the first position, and wherein the first and the second chromophores can be used for energy transfer; (b) exciting either the first or the second chromophore; and (c) measuring FRET between the chromophores; wherein a difference between FRET in the presence of the test compound and FRET in the absence of the test compound indicates that the test compound produces the desired effect, such that the energy transfer between the two chromophores is altered.

In another preferred embodiment, the ligands are covalently bound, linked, attached fused or otherwise in contact with a suitable donor or acceptor fluorophore.

In another preferred embodiment, the type of target molecule that can be assayed is not limited by its form, structure, and the medium it is assayed in. For example, the target molecule can be: free in solution, part of an intact cell, a permeabilized cell, a disrupted cell, a cell homogenate, a membrane, a cellular organelle, attached to beads, attached or bound to nanoparticles, lipids, columns, polymers, plastics, glass and the like. In some aspects, the sample is free floating and not attached to the surface of the cuvette or receptacle. Examples of types of molecules include without limitation: a protein, a peptide, a polypeptide, a nucleic acid, a polynucleotide, an oligonucleotide, a peptide nucleic acid, a glycoprotein, a carbohydrate, an organic or inorganic molecule, an isolated natural molecule, a synthetic molecule, small molecules, or combinations thereof.

In other embodiments, the target molecule can be attached to a lipid or cell membrane. Lipids suitable for methods and kits provided herein may be any lipids or a combination thereof in various ratios capable of forming a membrane known in the art. In certain embodiments, the lipids are naturally occurring. In certain embodiments, the lipids are synthetic. In certain embodiments, the lipids are one or more of fatty acyls, glycerolipids, glycerophospholipids, sphingolipids, saccharolipids, polyketides, sterol lipids, prenol lipids and a derivative thereof. In certain embodiments, the lipids are one or more of choline-based lipids (e.g., phosphatidylcholine (PC)), ethanolamine-based lipids (e.g., phosphatidylethanolamine (PE)), serine-based lipids (e.g., phosphatidylserine), glycerol-based lipids (e.g., phosphatidylglycerol), cholesterol-based lipids, dolichols, sphingolipids (e.g., sphingosine, gangliosides, or phytosphingosine), inositol-based lipids (e.g., phosphatidylinositol), cardiolipin, phosphatidic acid, lysophosphatides (e.g., lysophosphatides), hydrogenated phospholipids and a derivative thereof.

In certain embodiments, the lipids are one or more of PC, dioleoylphosphatidylcholine (DOPC), dimyristoylphosphatidylcholine (DMPC), dipalmitoylphosphatidylcholine (DPPC), distearoylphosphatidylcholine (DSPC), palmitoyl oleoylphosphatidylcholine (POPC), 2-dioleoyl-3-succinyl-sn-glycerol choline ester (DOSC), PE, dioleoylphosphatidylethanolamine (DOPE), dimyristoylphosphatidylethanolamine (DMPE), dipalmitoylphisphatidylethanolamine (DPPE), dioleoylphosphatidylserine (DOPS), dipalmitoyl-phosphatidylserine (DPPS), dioleoylphosphatidylglycerol (DOPG), dipalmitoylphosphatidylglycerol (DPPG), sphingomyelin (SM), sodium dodecyl sulphate (SDS), cholesterol (CHOL), cholesterol hemisuccinate (CHEMS), cholesterol-(3-imidazol-1-yl propyl)carbamate (CHIM), diacylglycerol hemisuccinate (DG-Succ), cholesterol sulphate (Chol-SO$_4$), dimethyldioctadecylammonium bromide (DDAB), dioleoylphosphatidic acid (DOPA), 1,2-dioleoyloxypropyl-3-dimethylhydroxyethylammonium chloride (DORI), 11,2-dioleoyl-3-trimethylammonium propane (DOTAP), N-(1-(2, 3-dioleoyloxy)-propyl)-N,N,N-triethylammonium chloride (DOTMA), 1,2-dimyristyloxypropyl-3-dimethylhydroxyethylammonium bromide (DMRIE), 1,2-dioleoyl-3-dimethylammonium propane (DODAP), N,N-dioleyl-N,N-dimethylammonium chloride (DODAC), 1,2-dioleoyl-3-dimethylhydroxyethylammonium bromide (DORIE), N-(1-(2,3-dioleyloxy)-propyl)-N-(2-(sperminecarboxamido)ethyl)-N, N-dimeth-ylammonium trifluoroacetate (DOSPA), 1-(2-(oleoyloxy)ethyl)-2-oleyl-3-(2-hydroxyethyl)imidazolinium chloride (DOTIM), N-(trimethylammonioacetyl)-didodecyl-D-glutamate chloride (TMAG), N,N-di-n-hexadecyl-N,N dihydroxyethylammoniumbromide (DHMHAC), N,N-di-n-hexadecyl-N-methyl-N-(2-hydroxyethyl)ammonium chloride (DHDEAB), N,N-myristoyl-N-(1-hydroxyprop-2-yl)-N-methylammoniumchloride (DMHMAC), 1,2-dioleoyl-3-(4'-trimethylammonio)butanoyl-sn-glycerol (DOTB), Synthetic Amphiphiles Interdisciplinary (SAINT lipids), 4,(2,3-bis-acyloxy-propyl)-1-methyl-1H-imidazole (DOIM), 2,3-bis-palmitoyl-propyl-pyridin-4-yl-amine (DPAPy), 3.beta.-(N—(N9,N9-dimethylaminoethane)carbamoyl)cholesterol (DC-Chol), 3.beta.-(N—(N9,N9-trimethylaminoethane)carbamoyecholesterol (TC-Chol), 3.beta.(N—(N,N-Dimethylaminoethan)-carbamoyl)cholesterol (DAC-Chol), cetyltrimethylammonium bromide (CTAB), cationic cardiolipins (e.g. (1,3-bis-(1,2-bis-tetradecyloxy-propyl-3-dimethylethoxyammoniumbromide)-p-ropane-2-ol) (NEOPHECTIN™), N-histidinyl-cholesterol hemisuccinate (HistChol), 4-(2-aminoethyl)-morpholino-cholesterol hemisuccinate (MoChol), histaminyl-cholesterol hemisuccinate (HisChol), and a derivative thereof.

Solvents suitable for methods and kits provided herein may be any solvent capable of facilitating lipid solubilization known in the art. In certain embodiments, the solvent is one or more of methanol, ethanol, acetonitrile and chloroform. In one embodiment, the solvent is methanol. In another embodiment, the solvent is ethanol. In yet another embodiment, the solvent is acetonitrile. In yet another embodiment, the solvent is chloroform. In certain embodiments, the solvent is an aqueous solution comprising one or more amphiphilic detergents. Examples of such detergents include, but are not limited to, oxylglucoside, octaethylene glycol monododecyl ether ($C_{12}E_8$), dodecylphosphocholine and deoxycholate.

Target Molecules:

Below is a non-exhaustive list of cellular macromolecules that represent therapeutic targets (also referred to herein as "target molecules") for HTS drug discovery using the methods described herein. The targets fulfill the criteria that the modulation of their amounts, function, expression and the like, will have a therapeutic effect in the context of a particular disease, and that they are not essential for the host or their amount can be decreased or increased without damage to the host. Alternatively, the targets may be present selectively or at higher levels in cells involved in a particular disease (for example a mutated or non mutated protein in cancer cells) such that the modulation of the amounts of the target will affect primarily those cells and not the entire host. Examples include, without limitation: Amyloid Precursor Protein (APP), the protein that is a precursor for the toxic Aβ aggregates found in Alzheimer's disease; mutated APP responsible for familial Alzheimer's disease; BACE-1, the β-site APP cleavage enzyme, which is one of the two enzymes leading to the formation of toxic Aβ aggregates; Tau, another key protein involved in Alzheimer's disease pathology and other diseases termed tauopathies; mutated tau responsible for inherited forms of frontotemporal dementia; hyperphosphorylated tau, the pathogenic form of the tau protein; α-synuclein, which, when overexpressed and/or aggregated, causes Parkinson's Disease and other diseases known collectively as synucleinopathies; mutated SOD1 responsible for familial amyotrophic lateral sclerosis (ALS); mutated huntingtin responsible for the inherited neurological disorder Huntington's disease; viral receptors or co-receptors such as the HIV co-receptor CCR5, which has been shown to be non-functional in humans naturally protected against HIV infection; oncogenes and anti-oncogenes; tumor cell markers that are linked to tumor invasiveness and metastatic potential; insulin receptor, the downregulation of which causes Type II diabetes; cytokine or chemokine receptors; enzymes of the ubiquitin pathway; enzyme markers and the like.

In some embodiments, desired target molecules are nucleic acids, candidate target sequences are first used to search several databases which catalog, for example, SNPs, sequences which regulate expression or function of an encoded product and the like. The targeted databases include NCBI's dbSNP, the UK's HGBASE SNP database, the SNP Consortium database, and the Japanese Millenium Project's SNP database.

In some embodiments, following dbSNP searches, gene loci databases (e.g., Locus Link) are searched. LocusLink provides a single query interface to curated sequence and descriptive information about genetic loci. It presents information on official nomenclature, aliases, sequence accessions, phenotypes, EC numbers, MIM numbers, UniGene clusters, homology, map locations, protein domains, and related web sites. The information output from LocusLink includes a LocusLink accession number (LocusID), an NCBI genomic contig number (NT#), a reference mRNA number (NM#), splice site variants of the reference mRNA (XM#), a reference protein number (NP#), an OMIM accession number, and a Unigene accession number (HS#).

In other embodiments, disease association databases can be searched to identify candidate target molecules. Following the LocusLink search, the information returned is used to search disease association databases. In some embodiments, the HUGO Mutation Database Initiative, which contains a collection of links to SNP/mutation databases for specific diseases or genes, is searched.

In some embodiments, the OMIM database is searched. OMIM (Online Mendelian Inheritance in Man) is a catalog of human genes and genetic disorders developed for the World Wide Web by NCBI, the National Center for Biotechnology Information. The database contains textual information and references. Output from OMIM includes a modified accession number where multiple SNPs are associated with a genetic disorder. The number is annotated to designate the presence of multiple SNPs associated with the genetic disorder.

In some embodiments, following dbSNP searches, software (e.g., including but not limited to, UniGene) is used to partition search results into gene-oriented clusters (e.g. gene oriented cluster analysis). UniGene is a system for automatically partitioning GenBank sequences into a non-redundant set of gene-oriented clusters. Each UniGene cluster contains sequences that represent a unique gene, as well as related information such as the tissue types in which the gene has been expressed and map location. In addition to sequences of well-characterized genes, hundreds of thousands novel expressed sequence tag (EST) sequences are included in UniGene. Currently, sequences from human, rat, mouse, zebrafish and cow have been processed.

In some embodiments, target sequences are used to search genome databases (e.g., including but not limited to the Golden Path Database at University of California at Santa Cruz (UCSC) and GenBank). The GoldenPath database is searched via BLAST using the sequence in FASTA format or using the RS# obtained from dbSNP. GenBank is searched via BLAST using the masked sequence in FASTA format. In some embodiments, GoldenPath and GenBank searches are performed concurrently with TSC and dbSNP searches. In some embodiments, the searches result in the identification of the corresponding gene. Output from GenBank includes a GenBank accession number. Output from both databases includes contig accession numbers. Thus, there are many ways one of skill in the art can identify a potential target, in addition to a user's desired target molecule.

Other target molecules may be selected, for example, in steroid hormone based therapies. In such cases, for example, sulfation, encompasses involvement in estrogen level regulation in mammary tumors, as well as androgen levels in prostate tumors. The availability of robust HTS assays for steroid sulfation may provide an important addition to the arsenal of molecular tools available to pharma groups focused on steroid signal transduction.

The modulation of neurosteroids is being investigated as a novel pharmacological approach to controlling neural excitatory balance (Malayev, A., et al., *Br J Pharmacol*, 2002, 135:901-9; Maurice, T., et al., *Brain Res Brain Res Rev*, 2001, 37:116-32; Park-Chung, M., et al., *Brain Res*, 1999, 830:72-87). The methods encompassed by the present invention may suitably accelerate these efforts by allowing facile screening of endogenous and synthetic neurosteroids for sulfoconjugation, offering insight into the fundamental biology as well as providing a tool for lead molecule identification and optimization. The need for better molecular tools is accentuated by the fact that there is already a sizeable over the counter market for DHEA as an "anti-aging" dietary supplement purported to alleviate age related senility and memory loss (Salek, F. S., et al., *J Clin Pharmacol*, 2002, 42).

In another example, the methods embodied in the present invention may suitably identify drug targets with respect to cholesterol sulfate in the regulation of cholesterol efflux, platelet aggregation and skin development in treatments for cardiovascular disease and perhaps some forms of skin cancer. In this instance, a sulfotransferase could become the drug target, and molecules that selectively inhibit this isoform may need to be identified.

In another example, a target molecule may be one involved in drug metabolism. Drug metabolism problems such as production of toxic metabolites and unfavorable pharmacokinetics cause almost half of all drug candidate failures during clinical trials. All of the major pharmaceutical companies have recognized the need to consider pharmacokinetic and pharmacogenomic consequences early in the drug discovery process resulting in an immediate need for high throughput in vitro methods for assessing drug metabolism. Aside from P450-dependent oxidation, glucuronidation is perhaps the most important route of hepatic drug metabolism. A broad spectrum of drugs are eliminated or activated by glucuronidation including non-steroidal anti-inflammatories, opioids, antihistamines, antipsychotics and antidepressants (Meech, R. and Mackenzie, P. I., *Clin Exp Pharmacol Physiol*, 1997, 24:907-15; Radominska-Pandya, A., et al., *Drug Metab Rev*, 1999, 31:817-99). Despite their importance, the broad and overlapping substrate specificity of the hepatic UDP-glucuronosyltransferases (UGTs) that catalyze glucuronidation remains poorly understood because of a lack of flexible in vitro assay methods.

In another example, the target molecule can be a protein kinase or a substrate thereof. There are more than 400 distinct kinases encoded in the human genome; elucidating their role in disease and identifying selective inhibitors is a major pharma initiative. Kinase malfunction has been linked to all of the most important therapeutic areas, including cancer, cardiovascular diseases, inflammation, neurodegenerative diseases, and metabolic disorders. Moreover, clinical validation of kinases as drug targets has recently been shown in the cases of Herceptin and Gleevec, which inhibit aberrant tyrosine kinases that contribute to breast cancer and leukemia, respectively. Embodiments of the methods will accelerate efforts to define kinase substrate specificity and to identify novel inhibitors by providing a universal catalytic assay that can be used with any kinase and any acceptor substrate.

Protein kinases are a large, diverse family with a key role in signal transduction. Protein kinases, which catalyze the transfer of the terminal phosphate group from ATP or GTP to serine, threonine or tyrosine residues of acceptor proteins, are one of the largest protein families in the human genome. In the broadest senses, they can be divided into serine/threonine or tyrosine kinases and soluble enzymes or transmembrane receptors. In the most recent and comprehensive genomic analysis, 428 human kinases were identified that comprise eight different homology groups, which also reflect differences in substrate specificity, structure/localization and/or mode of regulation (Hanks, S. K., *Genome Biol*, 2003, 4:111). For instance, there are 84 currently identified members of the Tyrosine Kinase group, which includes both transmembrane growth factor receptors such as EGFR and PDGFR and soluble enzymes such as the Src kinases, 61 currently identified members of the cyclic nucleotide dependent group, ser/thr kinases which includes the lipid dependent kinases—the PKC isoforms, and 45 currently identified members of the "STE" group, which includes the components of the mitogenic MAP kinase signaling pathway.

Kinases are ubiquitous regulators of intracellular signal transduction pathways, and as such have come under intense focus by pharmaceutical companies searching for more selective therapies for a broad range of diseases and disorders; they are second only to G-protein coupled receptors in terms of pharma prioritization (Cohen, P., *Nat Rev Drug Discov*, 2002, 1:309-15). Intracellular targets for phosphorylation include other kinases, transcription factors, structural proteins such as actin and tubulin, enzymes involved in DNA replication and transcription, and protein translation, and metabolic enzymes (Cohen, P., *Trends Biochem Sci*, 2000, 25:596-601). Phosphorylation can cause changes in protein catalytic activity, specificity, stability, localization and association with other biomolecules. Simultaneous phosphorylation at multiple sites on a protein, with different functional consequences, is common and central to the integration of signaling pathways.

Each kinase may phosphorylate one or more target proteins, sometimes at multiple sites, as well as autophosphorylate within one or more regulatory domains that control catalytic activity or interaction with other biomolecules. Defining the functional consequences of cellular phosphorylation profiles for normal and disease states is a major proteomics initiative. However, to use this knowledge for deciding which kinases to target for drug discovery, their specificity for acceptor substrates must also be delineated. Kinases recognize specific linear sequences of their target proteins that often occur at beta bends. In general, amino acids that flank the phosphorylated residue for three to five residues on either side define a phosphorylation site. The PhosphoBase database, which compiles known kinase phosphorylation sites, contains entries for 133 human kinases, less than a third of the total kinases. Moreover, most, if not all of these specificity profiles are incomplete, as they only show one or two peptides that have been identified as substrates for each kinase. Though there is significant overlap in substrate specificity among related kinases, there is no consensus sequence that is phosphorylated by a large number of kinases.

The biological rationale for targeting kinases to intervene in cancer is far too extensive to attempt an overview here. However, one of the dominant themes is the involvement of numerous kinases in controlling the delicate balance between the rate of cell division (cell cycle progression), cell growth (mass), and programmed cell death (apoptosis) that is perturbed in all cancers. Growth factor receptor tyrosine kinases (RTKs) are membrane-spanning proteins that transduce peptide growth factor signals from outside the cell to intracellular pathways that lead to activation of progrowth and anti-apoptotic genes. The majority of the fifty-eight RTKs in humans are dominant oncogenes, meaning that aberrant activation or overexpression causes a malignant cell phenotype. Not surprisingly, tyrosine kinases are being aggressively pursued as anticancer drug targets and both small molecule and monoclonal antibody inhibitors—GLEEVEC and HERCEPTIN, respectively—have been clinically approved. Downstream signaling from growth factor receptors occurs through multiple pathways involving both ser/thr and tyrosine kinases. One of the dominant kinases is the mitogen activated protein kinase (MAPK) pathway, which includes Raf and MEK kinases; inhibitors of all of these kinases are currently being tested in clinical trials (Dancey, J. and Sausville, E. A., *Nat Rev Drug Discov*, 2003, 2:296-313). Soluble tyrosine kinases, especially the 11 oncogenes that comprise the Src family, also transduce mitogenic signals initiated by RTKs and are being targeted by pharma (Warmuth, M., et al., *Curr Pharm Des*, 2003, 9:2043-59). Following mitogenic signals through RTKs that initiate entry into the G1 phase, progression through the cell cycle is regulated by sequential activation of phase-specific kinases in association with cyclin proteins. The cyclin dependent kinases represent yet another important group of kinases that pharma is pursuing in the hopes of inhibiting malignant cell proliferation (Elsayed, Y. A. and Sausville, E. A., Oncologist, 2001, 6:517-37).

Thus, the assays embodied herein, can be used to screen drug libraries for inhibitors or activators of protein kinases. It will also be useful for screening peptides or proteins as acceptor substrates for kinases. In these applications, it will have the significant advantages over other methods such as the universal nature of the assay, simplified homogenous assay, no radioactivity, and the ability to quantify enzyme turnover.

Depending on the target molecule, a test compound, identified by the methods embodied herein, would then be one that would be useful in the treatment of that disease or disorder for which the target molecule plays a role or directly contributes to the disease or disorder.

Förster Resonance Energy Transfer (FRET): FRET is a radiationless process in which energy is transferred from an excited donor molecule to an acceptor molecule. Radiationless energy transfer is the quantum-mechanical process by which the energy of the excited state of one fluorophore is transferred without actual photon emission to a second fluorophore. The quantum physical principles are reviewed in Jovin and Jovin, 1989, Cell Structure and Function by Microspectrofluorometry, eds. E. Kohen and J. G. Hirschberg, Academic Press. Briefly, a fluorophore absorbs light energy at a characteristic wavelength. This wavelength is also known as the excitation wavelength. In FRET, the energy absorbed by a fluorophore is subsequently transferred by a non-radiative process to a second fluorophore. The first fluorophore is generally termed the donor (D) and has an excited state of higher energy than that of the second fluorophore, termed the acceptor (A).

Critical features of the process are that the emission spectrum of the donor fluorophore overlap with the excitation spectrum of the acceptor, and that the donor and acceptor be sufficiently close. The distance between D and A must be sufficiently small to allow the radiationless transfer of energy between the fluorophores. Since the rate of energy transfer is inversely proportional to the sixth power of the distance between the donor and acceptor, the energy transfer efficiency is extremely sensitive to distance changes. Energy transfer is said to occur with detectable efficiency in the 1-10 nm distance range, but is typically 4-6 nm for optimal results. The distance range over which radiationless energy transfer is effective depends on many other factors as well, including the fluorescence quantum efficiency of the donor, the extinction coefficient of the acceptor, the degree of overlap of their respective spectra, the refractive index of the medium, and the relative orientation of the transition moments of the two fluorophores.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

A skilled artisan will recognize that many fluorophore molecules are suitable for FRET. A fluorophore is a fluorescent component, or functional group, bound to a molecule. A fluorophore can be a fluorescent molecule, a glowing bead, a glowing liposome, a quantum dot ("QD"), a fluorescent or phosphorescent nanoparticle ("NP"), a fluorescent latex particle or microbead. A fluorescent molecule can be fluorescein, carboxyfluorescein and other fluorescein derivatives, rhodamine, and their derivatives, or any other glowing entity capable of forming a covalent bond with the ligand.

In one embodiment, fluorescent proteins are used as fluorophores. A large variety of fluorophores are available and can find use in the methods described herein, for example and without limitation: ALEXA Fluors (Molecular Probes/Invitrogen) and DYLIGHT Fluors (Thermo Fisher Scientific). These fluorophores have an emission spectra that span a wide range, including ultraviolet, near-ultraviolet, visible, near-infrared, and infrared ranges. Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2-,2'-disulfonic acid derivatives, chelates of Lanthanide ions (e.g., Europium, Dysprosium, Samarium or Terbium). Representative acceptor fluorescent moieties, depending upon the donor fluorescent moiety used, include LC-Red 640, LC-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, allophycocyanin, XL665, d2. Donor and acceptor fluorescent moieties can be obtained, for example, from Molecular Probes (Junction City, Oreg.) or Sigma Chemical Co. (St. Louis, Mo.).

Certain naturally occurring amino acids, such as tryptophan, are fluorescent Amino acids may also be derivatized, e.g. by linking a fluorescent group onto an amino acid (such as linking AEDANS to a Cys), to create a fluorophore pair for FRET. The AEDANS-Cys pair is commonly used to detect protein conformational change and interactions. Some other forms fluorescence groups have also been used to modify amino acids and to generate FRET within the protein fragments (e.g. 2,4-dinitrophenyl-lysine with S—(N-[4-methyl-7-dimethylamino-coumarin-3-yl]-carboxamidomethyl)-cystein-e-).

In another embodiment, which is especially suitable for using in live cells, green fluorescent protein (GFP) and its various mutants are used as the fluorophores. Red fluorescent proteins such as DsRed (Clontech) having an excitation maximum of 558 nm and an emission maximum of 583 can also be used. Examples of fluorescent proteins are found in the Genbank and SwissPro public databases.

FRET between two different fluorophores can be assayed by several methods: looking at the change in color of the fluorescence, measuring the fluorescence lifetime of the donor, examining the changes upon photobleaching either the donor or acceptor or both donor/acceptor fluorphore. Regardless of the approach, most of these assays share common features of the instrumentation. Examples of such are the EnVision Plate Reader (Molecular Devices), ViewLux ultraHTS Microplate Imager (PerkinElmer), OPTIMA Microplate Readers, FLUOstar and POLARstar (BMG Labtech). Preferred measurement is by time-resolved fluorimetry.

FRET between two different fluorophores can be assayed by high-content cell screening using an instrument that detects changes in fluorescence in cells or in particular subcellular localizations. Examples of such instrumentation are the INCell Analyzer (GE Healthcare), ImageXpress Micro High Content Screening System (Molecular Devices), Opera, Operetta (PerkinElmer), Cellomics ArrayScan VTI HCS Reader (Thermo Scientific).

Instead of eliciting non-radiative energy transfer to an acceptor fluorophore by irradiating a donor fluorophore, it is possible to achieve a non-radiative transfer of energy from a donor enzyme to a complementary acceptor fluorophore after substrate oxidation. Such a process is called bioluminescence resonance energy transfer (BRET). Examples of donor enzymes are luciferase or aequorin, substrates can be luciferin or coelenterazine and the acceptor fluorophore can be GFP, YFP, EGFP, $GFP^2$ or GFP10 (Pfleger K. et al, *Nature Protocols,* 2006, 1, 337-345). BRET can be detected using a luminometer or scanning spectrometer.

Embodiments of the invention are also directed to various FRET assays, such as for example: steady-state FRET, Fluorescence Lifetime, Time-Resolved FRET, Intramolecular FRET or Intermolecular FRET. An example of Intramolecular FRET is one between two chromophores labeled within a single molecule (e.g. to identify conformational changes by a molecule). In certain embodiments, intramolecular FRET of a molecule can be measured in the absence of any other molecules. In certain embodiments, intramolecular FRET can be measured in the presence of one or more interacting proteins (e.g., any ligand-receptor interaction).

FRET as provided herein can also be detected intermolecularly, for example, between two or more chromophores labeled in two or more different molecules.

The Z' factor is used to assess the quality of the assay throughout development (Zhang J H et al. *J Biomol Screen.* 1999; 4(2):67-73). The Z' factor integrates the assay signal dynamic range (difference between the mean of the positive controls and the mean of the negative controls) and the statistical variability of the signals, and ranges from 0 (poor quality) to 1 (high quality). The higher the Z' value, the greater is the assay robustness, with values equal to or higher than 0.5 indicating an excellent assay. $Z'=1-[3\times(SD_{C+}+SD_{C-})/(Mean_{C+}-Mean_{S-})]$ where $SD_{C+}$=standard deviation of the positive control (maximum signal); $SD_{C-}$=standard deviation of the negative control (minimum signal); $Mean_{C+}$=mean value of the positive control; $Mean_{C-}$=mean value of the negative control.

Sample Containers:

Although described above as a cuvette, embodiments of the invention are effective in any number of receptacle, container or vessel geometries. Thus, the assays can be conducted in a tube, vial, dish, flow cell, cassette, cartridge, microfluidic chip, and any other similar type of containers. In other embodiments, the container can be composed of a plethora of materials, in any shape and of any type. Therefore, the assay format may also be applied to a flattened plastic or glass cassette or cartridge in which assay components might be magnetically pulled along a channel or path by an external magnet. Hence, several embodiments or geometries for the assay vessel are envisioned, including cuvettes having a translucent or open surface area pervious to irradiation at the exciting wavelength so as to enable a fluorescent assay. For example, the cuvette translucent surface area, may be formed as a square, rectangular, round, oval, or flat container, beads, vial, tube, cylinder, cassette, or cartridge. The preferred embodiment is a multiwall microtiter plate.

In embodiments, the receptacle comprises: a cuvette, multiwell plate, tube, flask, disk, beads, vial, cassette, flow cell, cartridge, microfluidic chip or combinations thereof, which permit irradiation at the wavelength of the donor fluorophore and measurement at the wavelength of the acceptor fluorophore.

In embodiments, the methods and assays described herein are provided in a high-throughput screening assay format. The benefits of such formats are easily identifiable, such as for example, screening of large patient samples for diagnostic or prognostic purposes, screening for new drugs, research, and the like.

Candidate/Test Agents:

Candidate agents include numerous chemical classes, though typically they are organic compounds including small organic compounds, nucleic acids including oligonucleotides, peptides or antibodies. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries:

Developments in combinatorial chemistry allow the rapid and economical synthesis of hundreds to thousands of discrete compounds. These compounds are typically arrayed in moderate-sized libraries of small molecules designed for efficient screening Combinatorial methods, can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci* USA. 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol. Divers.* 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci.* USA, 90:6909-6913 (1993)); vinylogous polypeptides (Hagihara, et al., *J. Amer. Chem. Soc.* 114:6568 (1992)); nonpeptidal peptidomimetics with .beta.-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

The screening assays of the invention suitably include and embody, animal models, cell-based systems and non-cell based systems. Identified genes, variants, fragments, or oligopeptides thereof are used for identifying agents of therapeutic interest, e.g. by screening libraries of compounds or otherwise identifying compounds of interest by any of a variety of drug screening or analysis techniques. The gene, allele, fragment, or oligopeptide thereof employed in such screening may be free in solution, affixed to a solid support, borne on a cell surface, or located intracellularly. The measurements will be conducted as described in detail in the examples section which follows.

In some embodiments, a method of identifying candidate therapeutic agents comprises screening a sample containing the specific target molecule in a high-throughput screening assay comprising the steps of: (i) adding a first and second ligand, each having a first and second detectable label, (ii) the first and second ligands each binding to separate and specific sites on a specific target molecule, wherein the screening assay optionally omits or does not require the step of (iii) washing and detecting an emission of light when the first and second ligands specifically bind to the specific target molecule.

In another preferred embodiment, a method of identifying therapeutic agents comprises contacting: (i) a target molecule with a candidate therapeutic agent; determining whether (i) the agent modulates a function of the peptide or interaction of the peptide with a partner molecule; or (ii) the agent modulates expression and/or function of the nucleic acid sequence of the target as measured by the light emission assays embodied herein.

In another preferred embodiment, a method of identifying candidate therapeutic agents for treatment of disease, comprises culturing an isolated cell expressing a target molecule, administering a candidate therapeutic agent to the cultured cell; correlating the target molecules expression, activity and/or function in the presence or absence of a candidate therapeutic agent as compared to control cells, wherein a drug is identified based on desirable therapeutic outcomes. For example, a drug which modulates expression of the target molecule whereby expression levels are responsible for the disease state or the target molecule modulates the activity or amount of another molecule whether upstream or downstream in a pathway. In other examples the assays measure kinase activity. In other examples, the assay measure binding partners. In other examples, the assay measures amounts of candidate therapeutic agents which provide a desired therapeutic outcome.

Another suitable method for diagnosis and candidate drug discovery includes contacting a test sample with a cell expressing a target molecule, and detecting interaction of the test agent with the target molecule, an allele or fragment thereof, or expression product of the target molecule an allele or fragment thereof.

In another preferred embodiment, a sample, such as, for example, a cell or fluid from a patient is isolated and contacted with a candidate therapeutic molecule. The genes, expression products thereof, are monitored to identify which genes or expression products are regulated by the drug.

High-Throughput Screening

The assays embodied herein are suitable for identifying and quantifying specific molecules in a sample. In addition, the assays can be used for drug screening in a high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with identified genes, or fragments thereof, and washed. Bound molecules are then detected by the methods embodied herein. Alternatively, non-neutralizing antibodies can be used to capture the peptide and immobilize it on a solid support.

The methods of screening of the invention comprise using screening assays to identify, from a library of diverse molecules, one or more compounds having a desired activity. For example, modulating the amount of a target molecule. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with isolated cells with modulated receptors, including the appropriate controls.

In one embodiment, screening comprises contacting each cell culture with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

The methods disclosed herein can be used for screening a plurality of test compounds. In certain embodiments, the plurality of test compounds comprises between 1 and 200,000 test compounds, between 1 and 100,000 test compounds, between 1 and 1,000 test compounds, between 1 and 100 test compounds, or between 1 and 10 test compounds. In certain embodiments, the test compounds are provided by compound libraries, whether commercially available or not, using combinatorial chemistry techniques. In certain embodiments, the compound libraries are immobilized on a solid support.

As discussed above, the target can be present in any substrate as the assay parameters can be manipulated or optimized for each type of substrate. For example, if the target is at the surface of or in a cell, or secreted by a cell, the following parameters would be determined: the optimal cell line, cell density, culture medium, serum concentration, final reagents volumes, compound incubation times (for example 12, 24, 36 or 48 hours). If the target is in a cell-free solution, the optimal composition of the solution can be determined as well as the range of concentrations of the positive control standard. Other parameters that can be determined are ligand concentrations, temperature of incubation and incubation times of the ligands (for example 1 to 4 hours). The set-up of the reading instrument, for example a time-resolved fluorimeter, is optimized for the measurement window and time delay, excitation parameters (e.g. number of flashes delivered), gain adjustment, and reader head positioning with respect to the receptacle. The proper pharmacological control, if available, needs to be determined.

High throughput screening can be used to measure the effects of drugs on complex molecular events such as signal transduction pathways, as well as cell functions including, but not limited to, cell function, apoptosis, cell division, cell adhesion, locomotion, exocytosis, and cell-cell communication. Multicolor fluorescence permits multiple targets and cell processes to be assayed in a single screen. Cross-correlation of cellular responses will yield a wealth of information required for target validation and lead optimization.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

Microarrays:

Identification of a nucleic acid sequence capable of binding to a target molecule can be achieved by immobilizing a library of nucleic acids onto the substrate surface so that each unique nucleic acid is located at a defined position to form an array. In general, the immobilized library of nucleic acids are exposed to a biomolecule or candidate agent under conditions which favored binding of the biomolecule to the nucleic acids. The nucleic acid array would then be analyzed by the methods embodied herein to determine which nucleic acid sequences bound to the biomolecule. Preferably the biomolecules would carry a pre-determined label for use in detection of the location of the bound nucleic acids.

An assay using an immobilized array of nucleic acid sequences may be used for determining the sequence of an unknown nucleic acid; single nucleotide polymorphism (SNP) analysis; analysis of gene expression patterns from a particular species, tissue, cell type, etc.; gene identification; etc.

In further embodiments, oligonucleotides or longer fragments derived from any of the polynucleotide sequences, may be used as targets in a microarray. The microarray can be used to monitor the identity and/or expression level of large numbers of genes and gene transcripts simultaneously to identify genes with which target genes or its product interacts and/or to assess the efficacy of candidate therapeutic agents in regulating expression products of genes that mediate, for example, neurological disorders. This information may be used to determine gene function, and to develop and monitor the activities of therapeutic agents.

Microarrays may be prepared, used, and analyzed using methods known in the art (see, e.g., Brennan et al., 1995, U.S. Pat. No. 5,474,796; Schena et al., 1996, *Proc. Natl. Acad. Sci.* U.S.A. 93: 10614-10619; Baldeschweiler et al., 1995, PCT application WO95/251116; Shalon, et al., 1995, PCT application WO95/35505; Heller et al., 1997, *Proc. Natl. Acad. Sci.* U.S.A. 94: 2150-2155; and Heller et al., 1997, U.S. Pat. No. 5,605,662). In other embodiments, a microarray comprises peptides, or other desired molecules which can be assayed to identify a candidate agent.

Utilities

In preferred embodiments, the assay provides a method of quantifying specific proteins in a biological sample, for example, a body fluid or a cell including molecules which are intra-cellular, extra-cellular or cell surface molecules.

In certain embodiments, the assay provides a method of diagnosing a disease or disorder comprising screening a biological sample from a patient in order to identifying and/or quantify a marker or molecule diagnostic of the particular disease or disorder. For example, a genetic marker, protein marker and the like.

In certain preferred embodiments, the screening is conducted using high-throughput screening allowing for simultaneous diagnosing of many subjects at the same time.

In another preferred embodiment, a method of identifying subjects at risk of developing a disease or disorder comprising screening a biological sample from a patient and identifying and/or quantifying a marker or molecule diagnostic of the particular disease or disorder.

In another preferred embodiment a method for screening candidate compounds for the treatment or prevention of a disease or disorder comprises contacting a sample with a candidate therapeutic agent and measuring the effects the compound has on a target. For example if it is a cellular product such as a receptor, the compound may regulate the receptor levels and the compound can then be further studied for any possible therapeutic effects (increase or decrease of the parameter being monitored e.g. expression, oxidation level, metabolic markers, viability or apoptic markers). An abnormal expression state of the target may be caused by pathology such as a metabolic or infectious disease, degenerative disease, cancer, genetic defects and/or a toxin.

Kits and Methods

The present invention further provides systems and kits (e.g., commercial therapeutic, diagnostic, or research products, reaction mixtures, etc.) that contain one or more or all components sufficient, necessary, or useful to practice any of the methods described herein. These systems and kits may include buffers, detection/imaging components, positive/negative control reagents, instructions, software, hardware, packaging, or other desired components. The kits are useful for quantifying a specific protein in a biological sample, as well as identifying that specific protein.

The kits provide useful tools for screening test compounds capable of modulating the effects of a compound on a target molecule. The kits can be packaged in any suitable manner to aid research, clinical, and testing labs, typically with the various parts, in a suitable container along with instructions for use.

Provided herein are kits for identifying and quantifying a specific molecule in a sample. In certain embodiments, the kits comprise (a) a target molecule labeled with a first chromophore; and (b) a test agent labeled with a second chromophore. In certain embodiments, the kits comprise (a) a test agent labeled with a first chromophore; and (b) a second test agent labeled with a second chromophore. In certain embodiments, the kits may further comprise lipids and/or solvents. In certain embodiments, the kits may further comprise buffers and reagents needed for the procedure, and instructions for carrying out the assay. In certain embodiments, the kits may further comprise, where necessary, agents for reducing the background interference in a test, positive and negative control reagents, apparatus for conducting a test, and the like.

In certain embodiments of the methods and kits provided herein, solid phase supports are used for purifying proteins, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

Methods and kits disclosed herein may be carried out in numerous formats known in the art. In certain embodiments, the methods provided herein are carried out using solid-phase assay formats. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (e.g., round- or flat-bottom multi-well plates). Exemplary multi-well plate formats that can be used in the methods provided herein include those found on 96-well plates (12×8 array of wells), 384-well plates (24×16 array of wells), 1536-well plate (48×32 array of well), 3456-well plates and 9600-well plates. Other formats that may be used in the methods provided herein include, but are not limited to, single or multi-well plates comprising a plurality of domains, cuvettes, microarrays etc. In certain embodiments, the plates are black-wall, black-bottom plates. In certain embodiments, the plates are black-wall, white-bottom plates. In certain embodiments, the plates have black walls and clear bottoms in order to allow bottom reading of the fluorescence signals. In certain embodiments, the plates are chosen with minimal and uniform intrinsic fluorescence intensity within the range utilized in the method to avoid interference with the FRET signals.

The methods provided herein, when carried out in standardized plate formats can take advantage of readily available equipment for storing and moving these plates as well as readily available equipment for rapidly dispensing liquids in and out of the plates (e.g., robotic dispenser, multi-well and multi-channel pipettes, plate washers and the like).

Administration of Compositions

The agents identified by the methods embodied herein can be formulated and compositions of the present invention may be administered in conjunction with one or more additional active ingredients, pharmaceutical compositions, or other compounds. The therapeutic agents of the present invention may be administered to an animal, preferably a mammal, most preferably a human.

The pharmaceutical formulations may be for administration by oral (solid or liquid), parenteral (intramuscular, intraperitoneal, intravenous (IV) or subcutaneous injection), transdermal (either passively or using ionophoresis or electroporation), transmucosal and systemic (nasal, vaginal, rectal, or sublingual), or inhalation routes of administration, or using bioerodible inserts and can be formulated in dosage forms appropriate for each route of administration.

The agents may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

The compounds identified by this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a cysteine protease. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiacetals, the conversion may be effected in accordance with conventional methods.

No unacceptable toxicological effects are expected when compounds, derivatives, salts, compositions etc., of the present invention are administered in accordance with the present invention. The compounds of this invention, which may have good bioavailability, may be tested in one of several biological assays to determine the concentration of a compound which is required to have a given pharmacological effect.

In another preferred embodiment, there is provided a pharmaceutical or veterinary composition comprising one or more identified compounds and a pharmaceutically or veterinarily acceptable carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The compounds identified by the methods herein would be suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference. Furthermore, one may administer the drug in a targeted drug delivery system, for example, in a liposome coated with a tissue-specific antibody. The liposomes will be targeted to and taken up selectively by the organ.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product.

The compound identified using these methods can be formulated according to known methods to prepare pharmaceutically useful compositions, whereby the compound is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™. (ICI Americas Inc., Bridgewater, N.J.), PLURONICS™. (BASF Corporation, Mount Olive, N.J.) or PEG.

The formulations to be used for in vivo administration must be sterile and pyrogen free. This is readily accomplished by filtration through sterile filtration membranes, prior to or following lyophilization and reconstitution.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

Formulations for oral administration in the present invention may be presented as: discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavoring agents such as peppermint, oil of wintergreen, cherry flavoring and the like can also be used. It may be desirable to add a coloring agent to make the dosage form readily identifiable. Tablets may also be coated by methods well known in the art.

A tablet may be made by compression or molding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavored base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile.

Dose:

An effective dose of a composition of the presently disclosed subject matter is administered to a subject in need thereof. A "therapeutically effective amount" or a "therapeutic amount" is an amount of a therapeutic composition sufficient to produce a measurable response (e.g., a biologically or clinically relevant response in a subject being treated). The response can be measured in many ways, as discussed above, e.g. cytokine profiles, cell types, cell surface molecules, etc. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

While various embodiments of the present invention have been described above, it should be understood that they have been presented by way of example only, and not limitation.

The following non-limiting examples are illustrative of the invention.

Example 1

Identification and Quantification of Prion Protein (PrP)—PrP-FEHTA

Materials and Methods

Best Ligand Pair Analysis.

A panel of ligands coupled to a fluorescent chromophore were tested for their capacity to bind the target at the cell surface or in solution. The ligands yielding a robust target-specific signal were selected. The absence of interference for binding to the target when the ligands were added simultaneously was then verified upon systematic pairing (one labeled "binding" ligand is mixed with one non-labeled "interfering" ligand). Finally, a best pair analysis was conducted in the following manner: the signal generated by any given ligand pair combination (one ligand being labeled with a donor chromophore and the other with an acceptor chromophore, and vice-versa) was measured for increasing concentrations of the target. The labeled ligand pair generating the strongest signal was retained.

Quantification of Recombinant PrP (rPrP) in Solution:

Recombinant PrP is added to the wells of a microtiter plate in phosphate buffer saline (PBS). PrP is immediately detected using PrP specific antibodies SAF32 (aa53-93) and D18 (aa133-157) labeled with the donor and acceptor fluorophores, respectively. PBS alone is used as a control for signal background. For data analysis, ratios (R) of the 665 nm (acceptor emission) to the 620 nm (donor emission) measurements are calculated.

Determination of PrP at the Cell Surface:

Cells are added to the wells of a microtiter plate. Compounds of a screening library are added, or the solvent control (usually DMSO) and the cells are incubated for 24 hours. Then, the amount of PrP present at the cell surface is detected on living cells. To detect cell surface PrP, antibodies are used as ligands. The best antibody pair is SAF32 directed against aa53-93 (Cayman Chemical) and D18 directed against aa133-157 (Williamson R. A., *J. Virol*, 1998, 72 (11), 9413-18) labeled with the donor and acceptor fluorophores, respectively. In this particular example, HTRF® was used, with Terbium cryptate as the donor fluorophore and d2 as the acceptor fluorophore. Antibodies were labeled by Cisbio. A PrP$^{0/0}$ cell line (KO) derived from primary hippocampal neurons of PrP gene-deficient mice serves as negative control for PrP expression. Blanks consist in culture medium in the absence of cells. For data analysis, ratios (R) of the 665 nm (acceptor emission) to the 620 nm (donor emission) measurements are calculated, to correct for non-specific absorption of 620 nm light by the assay mix. The value for the specific signal of the sample or positive control is given by Delta F %=$[(R_{C+}-R_{C-})/R_{C-}]\times100$ where $R_{C+}$ and $R_{C-}$ are the 665/620 ratios of the positive and negative control. This ratiometric measurement allows to correct for fluorescence interference induced by the assay matrix or screening compounds.

Cell Line:

LD9 cells, a fibroblastic cell line (Mahal S. et al. *Proc Natl Acad Sci* USA. 2007; 104(52):20908-13). This cell line presents reduced shedding of PrP into the medium and therefore less background signal for PrP when compared to neuroblastoma cells.

Pharmacological Control:

Brefeldine A (BFA), a compound that prevents trafficking of proteins from the ER to the Golgi (Nebenfuhr A. et al. *Plant physiology*. 2002; 130: 1102-8).

Other Assay Conditions:

Optimal incubation times are 24 hours for the compound, 3 hours for the antibody. Optimal antibody concentrations (dubbed 1×) are 0.33 µg/ml (D18-d2) and 0.036 µg/ml (SAF32-Tb).

Results and Discussion

Figure 3:
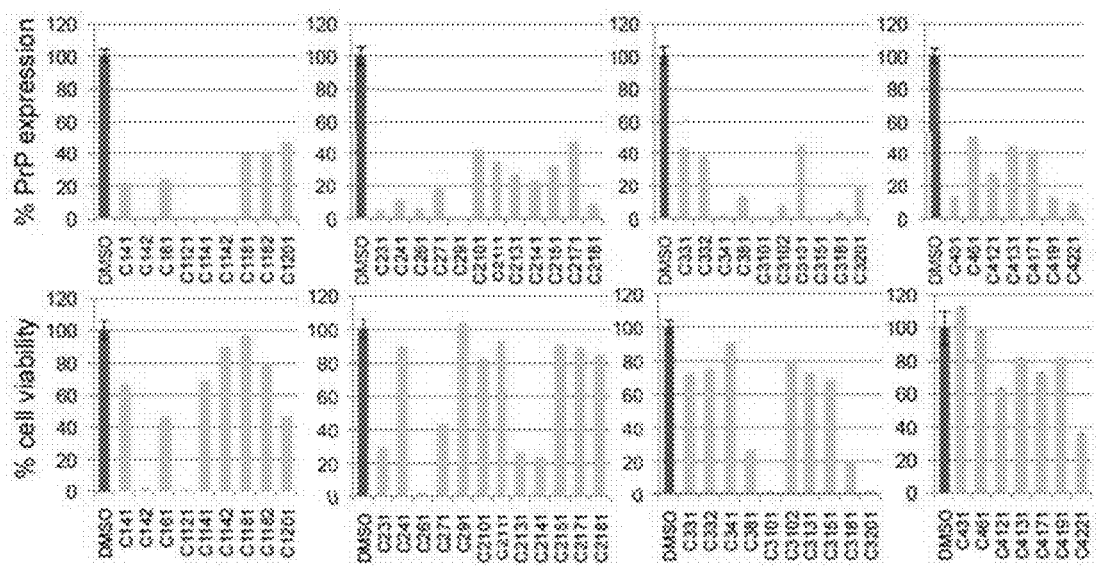
FIG. 3 is a graph showing results from the preliminary screening of the US Drug Collection using the primary screening assay. Only data from the candidate hits are shown (selected by using 50% reduction of cell surface PrP expression as a threshold). Upper panels show PrP expression at the surface of LD9 cells after treatment during 24 hours with the compounds indicated in the abscissa. PrP levels are expressed as a percentage of the DMSO control. Each screening plate is shown as a separate panel. DMSO control is shown in purple for each plate. BFA control reduced cell-surface PrP to background (0% PrP expression). Z' was 0.7 for all four plates. Lower panels show viability of LD9 cells treated with the compounds for 24 hours at the screening dose. Cell viability was measured by our counter-screening assay using the CELLTITER-GLO kit. Nine compounds exhibited less than 10% toxicity and were selected as hits.
Figures 4A, 4B, 4C, 4D:
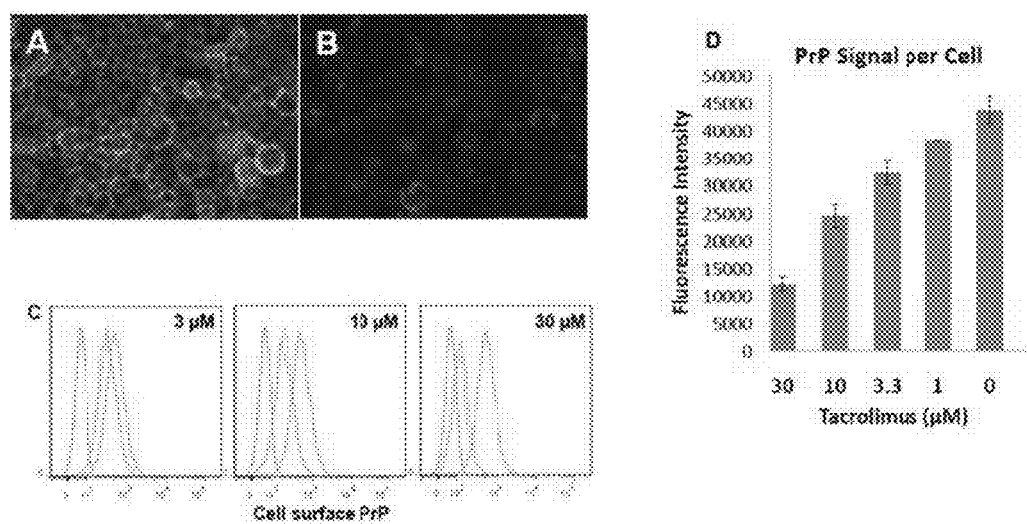
FIGS. 4A to 4D show the reduction of cell surface PrP by one of the hits, Tacrolimus, confirmed by secondary screening on N2a cells. PrP was labeled at the surface of living cells at +4° C. with monoclonal antibody D18 and fixed with 4% PFA prior to the addition of the Alexa-488 labeled secondary antibody.

With the assay in the 384-well format, the US Drug Collection was screened, a 1280-compound library comprising mainly FDA-approved drugs. The library was screened at a 20 µM concentration. Thirty-eight compounds reduced PrP expression by more than 50%, which was chosen as the screening threshold. The library was then counter-screened using a cell viability assay to reveal the toxic compounds. Nine out of the 38 candidate hits exhibited less than 10% toxicity and were considered hits (FIG. 3). Therefore the hit rate was 0.7%.

To confirm the hits, cell surface PrP levels were measured by an independent method. Cells were exposed to the compounds, washed with PBS, labeled at +4° C. with monoclonal antibody D18 for one hour, then fixed with 4% PFA prior to the addition of the Alexa-488 labeled secondary antibody to reveal the PrP antibody. Reduction of cell surface PrP can then be visualized under the epifluorescence microscope and quantified either by flow cytometry or with a high content subcellular analysis system such as the IN Cell Analyzer 1000 or 2000 (GE Lifesciences). Six of nine hits were confirmed, demonstrating that the primary assay yields hits that reproducibly reduce PrP levels at the cell surface. Moreover, as the final target of prions in the living organism is the brain, it is important to show the activity of compounds on a type of cells close to neuronal cells. All six compounds reduced PrP levels on neuroblastoma cells (N2a). The activity of Tacrolimus is shown in FIGS. 4A-4D as an example. Tacrolimus reduced PrP by 70% at 20 µM in the primary assay (on LD9 cells), and by 75 and 73% at 30 in the secondary assay (on N2a cells) by flow cytometry and IN Cell analyzer quantification, respectively.

Figures 5A, 5B:
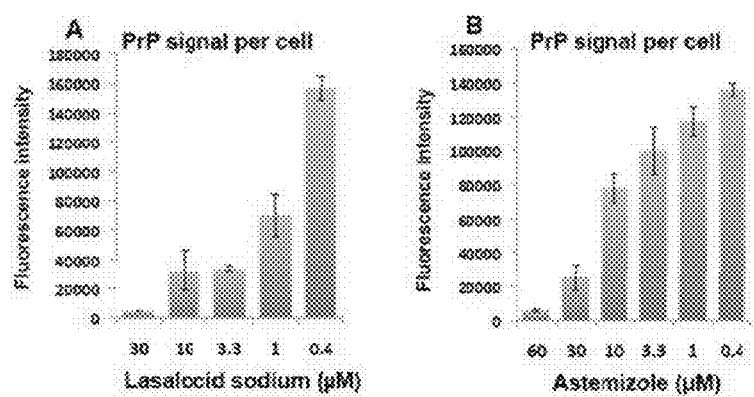
FIGS. 5A to 5B are graphs showing the reduction of cell surface PrP by two other hits, Lasalocid sodium and Astemizole, confirmed by secondary screening on N2a cells. PrP labeling and IN Cell Analyzer quantification were performed as described in FIGS. 4A-4D.
Figures 8A, 8B, 8C, 8D, 8E:
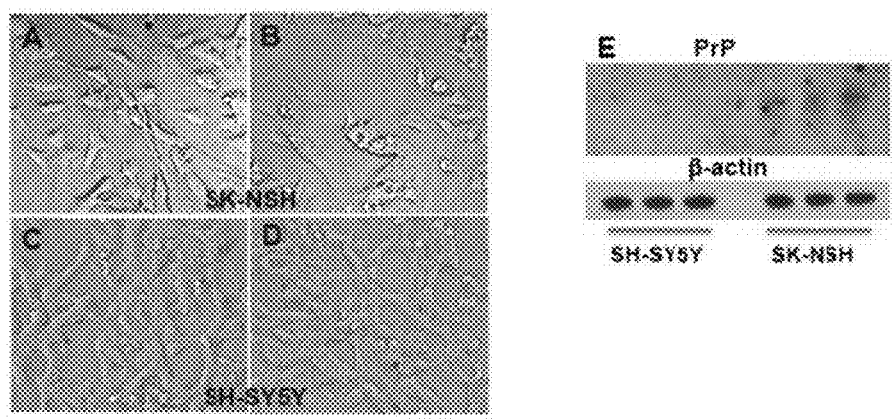
FIGS. 8A-8E show the toxicity of Aβ oligomers for human neuroblastoma cells restricted to those expressing PrP.

Other active compounds were Astemizole, Lasalocid sodium, Monensin, Emetine and cetrimonium. Quantification of PrP reduction by Astemizole and Lasalocid sodium is shown in FIGS. 5A and 5B. These compounds were subjected to further selection by counter-screening and prioritization as described below.

Counter-Screening:

Toxic compounds generate an artifactual decrease in the intensity of cell surface PrP signal and are excluded. The high-throughput luminescent cell viability assay, CELLTITER-GLO® (Promega) can be used to this purpose as shown in FIG. 3. Addition of the CELLTITER-GLO® reagent results in cell lysis and generation of a luminescent signal at 610 nm proportional to the amount of ATP, reflecting the number of living cells in culture.

Compound Prioritization:

To select the best compounds from the hits generated during the primary screening, the following strategy can be used: (1). Selection of the compounds exerting the highest PrP reducing effect. (2). Selection of the compounds exerting the PrP reducing effect at the lowest concentration and harboring the least toxicity on neuronal cells. To this end, $EC_{50}$ and $TC_{50}$ have to be determined on N2a cells using, for example, the assays described above (IF and Cell Titer Glo). (3). Selection of the compounds exhibiting the highest specificity for PrP. Although complete specificity for PrP is not required for a compound to achieve a good therapeutic index, this can be used as criteria for compound selection. Other markers expressed at the surface of neurons, such as, but not restricted to, amyloid precursor protein (APP) and CD24 (also called heat-stable antigen or nectadrin) are detected by IF using the same methodology as that used to detect cell surface PrP. After treatment of the cells with the compound, the extent of reduction of other proteins is compared with that of PrP. (4). Selection of the compounds showing the highest capacity to cure prion-infected cells and to prevent cellular infection by prions. Selected compounds can be tested for their capacity to inhibit prion replication in prion-infected cells using a Western blot or the Scrapie Cell Assay (SCA) (Kloehn P. C. et al, *Proc Natl Acad Sci* USA. 2003; 100(20):11666-71). These assays detect infected cells by virtue of their PrP$^{Sc}$ content. The total PrP$^{Sc}$ content of the cell culture can be measured by Western blot of cell lysates; infected cells can be recorded as "spots" in the SCA). FIG. 6 illustrates the curing effect of RML scrapie-infected PK1 cells by the enzyme phosphatidylinositol phospholipase C (PIPLC), an enzyme that cleaves off GPI-anchored proteins, hence PrP, from the cell surface, at 1 µg/ml, a concentration that removes approximately 50% of cell surface PrP. FIGS. 7A and 7B illustrate that tacrolimus (Tac) and astemizole (Ast), two compounds screened using the method described herein that reduce cell surface PrP amounts as shown in FIGS. 4A-4D and 5A-5B, block infection of PK1 neuroblastoma cells by RML and 22L prions. PK1 cells were pretreated for 3 days with the indicated doses of drugs and infected with RML (FIG. 7A) or 22L (FIG. 7B) prions using a $10^{-4}$ dilution of brain homogenate from an RML- or 22L-infected mouse. Treatment was continued for 12 days after infection. Cells were analyzed by western blot for proteinase K-resistant PrP$^{Sc}$ (a hallmark of prion infection) 9 and 18 days post-infection (i.e. 3 days before and 6 days after treatment cessation). PPS (pentosan polysulfate), a drug that prevents prion infection, was used at the dose of 10 µg/ml as positive control for treatment efficacy. CTRL:

untreated cells. Both astemizole and tracrolimus blocked prion infection, and there was no rebound of infectivity after treatment cessation.

These methods to screen for molecules inhibiting cell surface PrP expression have implications beyond the field of prion diseases. Indeed, PrP has been shown to mediate Aβ oligomer-induced neurotoxicity (Kudo et al., *Hum. Mol. Genet.* 21(5):1138-1144 (2012)) and memory impairment in transgenic Alzheimer mice (Lauren et al, *Nature* 2009; 457(7233):1128-32, Gimbel et al., *J. Neurosci.* 30(18):6367-6374 (2010)). Therefore compounds reducing PrP amounts may prevent Aβ-induced neurodegeneration in Alzheimer's disease. FIGS. 8A-8E show that Aβ oligomers are toxic for SK-NSH cells, but not for SH-SY5Y, the SK-NSH-derived cell line that does not express PrP or expresses undetectable levels thereof.

Example 2

Identification and Quantification of Tau Protein (Tau-FEHTA)

Another non-limiting example illustrative of the invention is provided. Here the microtubule-associated protein tau (MAPT, or tau) is being detected. Tau is a protein expressed primarily, but not exclusively, in the central and peripheral nervous system. Under physiological conditions, tau is subject to several posttranslational modifications including phosphorylation. It is believed to be a multifunctional protein involved in regulating the stability of microtubules and modulation of signaling pathways. Abnormally phosphorylated tau is involved in the pathogenesis of Alzheimer's disease and other neurodegenerative diseases collectively termed tauopathies. Hyperphosphorylated tau dissociates from microtubules and forms aggregates referred to as neurofibrillary tangles in Alzheimer's disease. Reduction or deletion of endogenous tau ameliorates synaptic and cognitive impairments in several mouse models of Alzheimer's disease (Roberson et al., *Science,* 2007, 316:750-754; Ittner et al. Cell, 2010, 142:387-397; Roberson et al., *J. Neurosci.,* 2011, 31:700-711) and rescues neuronal loss in a mouse model of Alzheimer's disease (Leroy et al., *Am. J. Pathol.,* 2012, 181:1928-1940). Therefore both reduction of overall tau as well as reduction of hyperphosphorylated tau would be beneficial for the treatment of Alzheimer's disease and other tauopathies.

Quantification of Intracellular Tau:

SH-SY5Y or SK-NSH cells were added to the wells of a microtiter plate. Compounds of a screening library were added, or the solvent control (usually DMSO) and the cells were incubated for 24 hours. Then, cells were lysed, for example, by the addition of concentrated lysis buffer and the amount of intracellular tau was detected. In this particular example, tau was detected using human tau specific antibodies directed against aa159-163 (0.05 µg/ml) and aa16-46 (1 µg/ml) labeled with the donor and acceptor fluorophores, respectively. Antibody incubation time was 60-90 minutes. HTRF® was used, with Terbium cryptate as the donor fluorophore and d2 as the acceptor fluorophore. Blanks consist in culture medium in the absence of cells. For data analysis, ratios (R) of the 665 nm (acceptor emission) to the 620 nm (donor emission) measurements were calculated, to correct for non-specific absorption of 620 nm light by the assay mix. The value for the specific signal of the sample or positive control is given by Delta F %=$[(R_{C+}-R_{C-})/R_{C-}]\times 100$ where $R_{C+}$ and $R_{C-}$ are the 665/620 ratios of the positive and negative control (blank). This ratiometric measurement allows to correct for fluorescence interference induced by the assay matrix or screening compounds.

Tau Knock-Down:

SH-SY5Y cells were plated at 70-80% confluence in wells of a E-well microtiter plate. Transfection with [SMARTpool: ON-TARGETplus MAPT siRNA] as well as [ON-TARGETplus Non-targeting Pool] as control siRNA (5 µM) was performed according to the manufacturer's instructions using the transfection reagent DHARMAFECT 2 (Thermo Fisher Scientific Biosciences Inc, 5 µl per well). Cells were lysed at day 3 post-transfection and cell lysates plated in 384-well microtiter plates for Tau quantification.

Figures 9A, 9B, 9C:
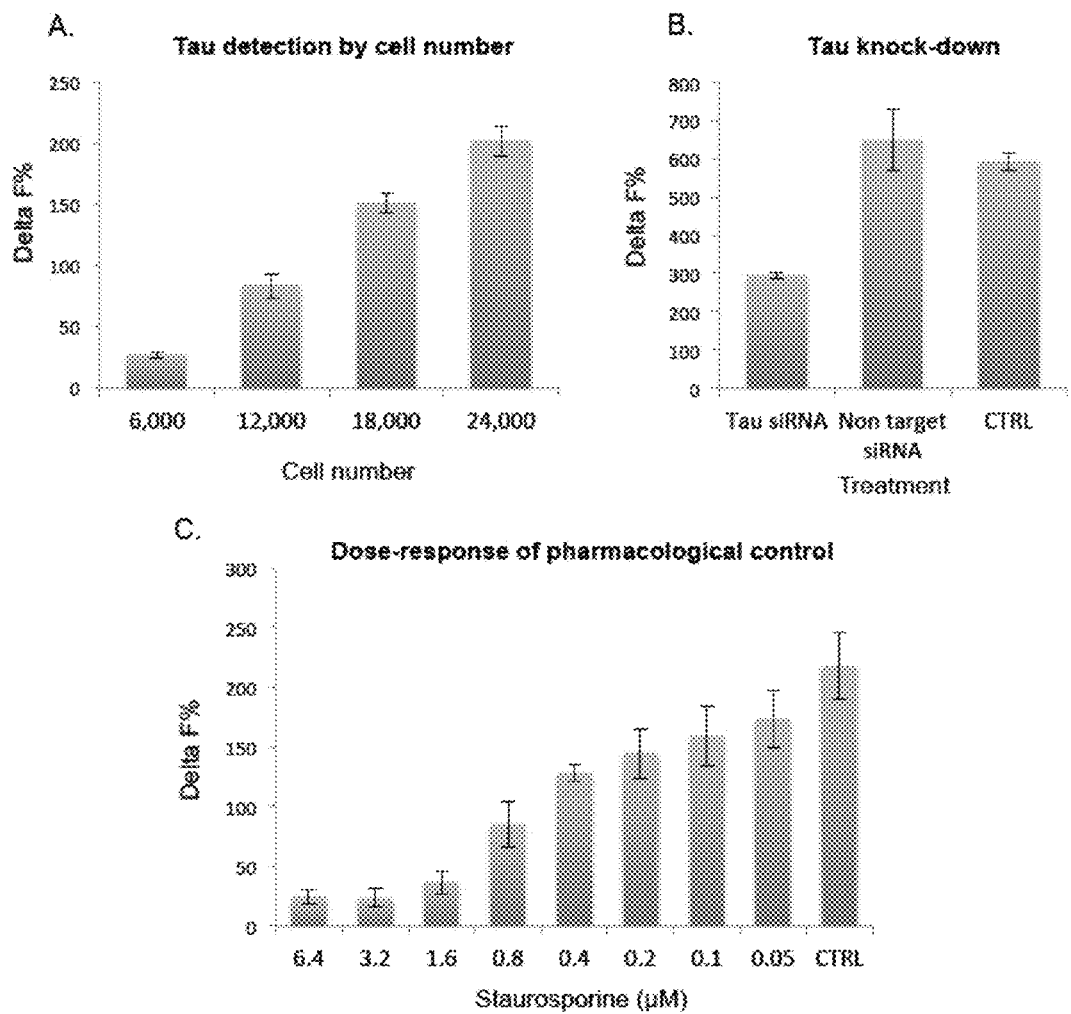
FIGS. 9A-9C are graphs showing detection of the tau protein in human neuroblastoma cells using the tau detection assay in the 384-well format. Tau levels are expressed as [Delta F %] which is a value resulting from the ratiometric measurement of the HTRF signal corresponding to the detection of tau.

Pharmacological Control:

Staurosporine was used as a control for the reduction of the amounts of Tau protein produced in the cell culture. Staurosporine was a kinase inhibitor inducing cell apoptosis at the concentrations used in FIG. 9C.

Compound Prioritization:

To select the best compounds from the hits generated during the primary screening, the following strategy can be used: (1). Selection of the compounds exerting the highest tau reducing effect, confirmed using an orthogonal assay. (2). Selection of the compounds exerting the tau reducing effect at the lowest concentration and harboring the least toxicity on neuronal cells. To this end, $EC_{50}$ and $TC_{50}$ were determined. (3). Selection of the compounds exhibiting the highest specificity for tau compared to other intracellular proteins. After treatment of the cells with the compound, the extent of reduction of other proteins was compared with that of tau. (4). Selection of compounds effective in primary neuronal cell cultures or neurons derived from differentiation of stem cells or induced pluripotent stem cells (iPSCs). (5). Medicinal chemistry analysis to select scaffolds lacking undesirable substructures that could hinder optimization efforts due to anticipated toxicity and/or potential for poor drug metabolism and pharmacokinetic (DMPK) properties, in particular with regards to passing the blood-brain-barrier (6). Selection of compounds according to their mode of action.

In particular, a modification of the assay can be performed to enable specific quantification of hyperphosphorylated tau. In this case, the assay made use of one or two ligands specific for the hyperphosphorylated form of the tau protein.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the Disclosure is provided to allow the reader to quickly ascertain the nature of the technical disclosure. It is submitted with the understanding that it will not be used to interpret or limit the scope or meaning of the following claims.

What is claimed is:

1. A method of identifying and quantifying a specific target molecule in a sample comprising:
   testing and selecting a first ligand or a plurality of first ligands and a second ligand or a plurality of second ligands coupled to a detectable label for binding to a target molecule; or, selecting a first ligand or a plurality of first ligands and a second ligand or a plurality of second ligands coupled to a detectable label for binding to a target molecule;

screening a sample containing the specific target molecule in a high-throughput screening assay comprising the steps of: (i) Adding a first and a second ligand, wherein the first ligand comprises a first detectable label and the second ligand comprises a second detectable label, (ii) the first and second ligands each binding to separate and specific sites on a specific target molecule, wherein the screening assay does not require the step of (iii) washing;

detecting an emission of light when the first and second ligands specifically bind to the specific target molecule; thereby, identifying and quantifying the specific target molecule in a sample.

2. The method of claim 1, wherein the detectable label comprises: fluorophores, luminescent molecules, enzymes or radionuclides.

3. The method of claim 1, wherein the light comprises: fluorescence, chemiluminescence, or bioluminescence.

4. The method of claim 1, wherein the first or second ligands comprise: antibodies, antibody fragments, Fv fragments; single chain Fv (scFv) fragments; Fab' fragments; F(ab')$_2$ fragments, humanized antibodies and antibody fragments; camelized antibodies and antibody fragments, human antibodies and antibody fragments, monospecific or bispecific antibodies, disulfide stabilized Fv fragments, scFv tandems ((scFv) fragments), diabodies, tribodies or tetrabodies, peptoids, peptide or nucleic acid aptamers, antibody mimetics or combinations thereof.

5. The method of claim 1, wherein the method is a high-throughput screening assay comprising a Førster Resonance Energy Transfer (FRET), Bioluminescence Resonance Energy Transfer (BRET), or fluorescence polarization assay.

6. The method of claim 1, where the specific target molecule comprises: a glycoprotein, a lipoprotein, a lipid, a protein fragment, a protein, protein fragments, peptides, a peptide nucleic acid, synthetic or natural macromolecules.

7. The method of claim 1, wherein the specific target molecule is present in a sample comprising: a liquid, a semi-liquid, a gel, a biological sample, an intact cell, a permeabilized cell, a disrupted cell, a cell homogenate, a membrane, or a cellular organelle.

8. The method of claim 1, wherein the first and second ligands comprise: a polypeptide, antibodies, antibody fragments, antibody mimetics, single chain antibodies, nucleic acids, an aptamer, a peptoid or a sugar moiety or combinations thereof.

9. The method of claim 8, wherein the first and second ligands are peptide or nucleic acid aptamers.

10. The method of claim 8, wherein the first and second ligands are sugar moieties comprising glycosaminoglycans, heparan sulfates or chondroitin sulfates.

11. A method of quantifying a specific protein in a sample, the method comprising the steps of:

placing the sample containing the specific target molecule into a receptacle permitting irradiation of the sample at a wavelength suitable for exciting the donor fluorophore and measurement of the fluorescence of the acceptor fluorophore via a high-throughput assay;

adding a first ligand that binds to a specific site on the target molecule wherein the first ligand is linked to a first fluorophore (the "donor fluorophore");

adding a second ligand that binds to a specific site on the same target molecule distinct from that to which the first ligand binds wherein the second ligand is linked to a second fluorophore (the "acceptor fluorophore");

irradiating the sample containing the target molecule linked to the ligands at a wavelength optimal for exciting the donor fluorophore and measuring the intensity of the light emitted by the acceptor fluorophore; thereby, quantifying the specific protein.

12. The method of claim 11, wherein the intensity of the light emitted is measured by time resolved fluorimetry.

13. The method of claim 11, wherein the target molecule is not attached to a support surface.

14. The method of claim 11, wherein the target molecule is attached to a support surface.

15. The method of claim 11, wherein excitation is transferred to the acceptor fluorophore when the acceptor fluorophore is at a distance from the donor fluorophore that is equal to or less than the distance defined by the Førster radius.

16. The method of claim 11, wherein the receptacle comprises: a cuvette, multiwell plate, tube, flask, disk, beads, vial, cassette, flow cell, cartridge, microfluidic chip or combinations thereof, which permit irradiation at the wavelength of the donor fluorophore and measurement at the wavelength of the acceptor fluorophore.

17. The method of claim 11, where the target molecule comprises: a glycoprotein, a lipoprotein, a lipid, a protein fragment, a protein, peptides, a peptide nucleic acid, synthetic or natural macromolecules.

18. The method of claim 11, wherein the target is present in a sample comprising: a liquid, a semi-liquid, a gel, a biological sample, an intact cell, a permeabilized cell, a disrupted cell, a cell homogenate, a membrane, or a cellular organelle.

19. The method of claim 11, wherein the first and second ligands that specifically bind to distinct, non-overlapping sites ("epitopes") on the target, comprise: antibodies or epitope binding antibody fragments, single chain antibodies, antibody mimetics, peptoids, aptamers, polypeptides or nucleic acids.

20. The method of claim 11, wherein the first and second ligands comprise: a polypeptide, an aptamer, a peptoid or a sugar moiety or combinations thereof.

21. The method of claim 20, wherein the first and second ligands are peptide or nucleic acid aptamers.

22. The method of claim 20, wherein the first and second ligands are sugar moieties comprising as glycosaminoglycans, heparan sulfates or chondroitin sulfates.

23. The method of claim 11, wherein the method is a high-throughput screening assay comprising a Førster Resonance Energy Transfer (FRET), Bioluminescence Resonance Energy Transfer (BRET), or fluorescence polarization assay.

24. A method of screening for a candidate therapeutic compound comprising:

screening a sample containing a specific target molecule in a high-throughput screening assay comprising the steps of: (i) contacting the sample with the candidate therapeutic compound (ii) Adding a first and a second ligand, wherein the first ligand comprises a first detectable label and the second ligand comprises a second detectable label, (iii) the first and second ligands each binding to separate and specific sites on a specific target molecule, wherein the screening assay does not require the step of (iv) washing;

detecting an emission of light when the first and second ligands specifically bind to the specific target molecule;

selecting the compound(s) that modulate(s) the amount of the target molecule as compared to a control; thereby, screening for a candidate therapeutic compound.

25. The method of claim 24, wherein the candidate therapeutic agent modulates an amount, function, activity or expression of a target molecule as measured by the emission of light.

26. A method of screening for a candidate therapeutic compound, the method comprising the steps of:

placing the sample containing a specific target molecule into a receptacle permitting irradiation of the sample at a wavelength suitable for exciting the donor fluorophore and measurement of the fluorescence of the acceptor fluorophore via a high-throughput assay;

contacting the sample with the candidate therapeutic compound;

adding a first ligand that binds to a specific site on the target molecule wherein the first ligand is linked to a first fluorophore (the "donor fluorophore");

adding a second ligand that binds to a specific site on the same target molecule distinct from that to which the first ligand binds wherein the second ligand is linked to a second fluorophore (the "acceptor fluorophore");

irradiating the sample containing the target molecule linked to the ligands at a wavelength optimal for exciting the donor fluorophore and measuring the intensity of the light emitted by the acceptor fluorophore;

selecting the compound(s) that modulate(s) the amount of the target molecule as compared to a control; thereby, screening for a candidate compound.

27. The method of claim 26, wherein the candidate therapeutic agent modulates an amount, a function, activity or expression of a target molecule as measured by the emission of light.

28. A method of diagnosing a disease or disorder comprising:

screening a biological sample from a patient by the method of claim 1 or 11;

identifying and/or quantifying a marker or molecule diagnostic of the particular disease or disorder; and, diagnosing the disease or disorder.

29. A method of identifying subjects at risk of developing a disease or disorder comprising:

screening a biological sample from a patient by the method of claim 1 or 11;

identifying and/or quantifying a marker or molecule diagnostic of the particular disease or disorder; and, identifying subjects at risk of developing the disease or disorder.

30. The method of claim 26, wherein the target molecule is a prion protein (PrP) or fragments thereof.

31. The method of claim 26, wherein the target molecule is a Tau protein or fragments thereof.

32. The method of claim 30, wherein a candidate therapeutic agent comprises: Astemizole, Tacrolimus, Lasalocid sodium, Monensin sodium, Emetine or Cetrimonium.

* * * * *